(12) United States Patent
Wauer et al.

(10) Patent No.: US 12,121,616 B2
(45) Date of Patent: Oct. 22, 2024

(54) TRANSDERMAL THERAPEUTIC SYSTEM FOR THE TRANSDERMAL ADMINISTRATION OF SOLIFENACIN

(71) Applicant: LTS LOHMANN THERAPIE-SYSTEME AG, Andernach (DE)

(72) Inventors: Gabriel Wauer, Bad Neuenahr-Ahrweiler (DE); Frank Seibertz, Bad Breisig (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 965 days.

(21) Appl. No.: 17/048,036

(22) PCT Filed: Apr. 11, 2019

(86) PCT No.: PCT/EP2019/059347
§ 371 (c)(1),
(2) Date: Oct. 15, 2020

(87) PCT Pub. No.: WO2019/201755
PCT Pub. Date: Oct. 24, 2019

(65) Prior Publication Data
US 2021/0161832 A1    Jun. 3, 2021

(30) Foreign Application Priority Data

Apr. 17, 2018  (DE) .................... 10 2018 205 840.7

(51) Int. Cl.
*A61F 13/02*    (2024.01)
*A61K 9/70*    (2006.01)
(Continued)

(52) U.S. Cl.
CPC ........ *A61K 9/7061* (2013.01); *A61F 13/0276* (2013.01); *A61K 9/7053* (2013.01);
(Continued)

(58) Field of Classification Search
CPC ... A61K 9/7084; A61K 9/7038; A61K 9/7092
See application file for complete search history.

(56) References Cited

U.S. PATENT DOCUMENTS

| | | | |
|---|---|---|---|
| 5,770,219 A * | 6/1998 | Chiang | A61K 31/57 424/448 |
| 2005/0181031 A1 * | 8/2005 | Saito | A61P 13/00 424/448 |
| 2005/0287194 A1 * | 12/2005 | Grenier | A61K 9/0014 514/588 |

(Continued)

FOREIGN PATENT DOCUMENTS

| | | |
|---|---|---|
| EP | 2599847 A1 | 6/2013 |
| EP | 3081211 A1 | 10/2016 |

(Continued)

OTHER PUBLICATIONS

International Search Report and Written Opinion for International Application No. PCT/EP2019/059347, European Patent Office, Netherlands, mailed on Jun. 27, 2019, 10 pages.
(Continued)

*Primary Examiner* — Sarah Al Hashimi
*Assistant Examiner* — Arjuna P Chatrathi
(74) *Attorney, Agent, or Firm* — STERNE, KESSLER, GOLDSTEIN & FOX P.L.L.C.

(57) ABSTRACT

The present invention relates to transdermal therapeutic systems (TTS) for the transdermal administration of solifenacin.

21 Claims, 3 Drawing Sheets

(51) Int. Cl.
*A61K 31/27* (2006.01)
*A61K 31/4748* (2006.01)
*A61K 47/14* (2017.01)
*A61K 47/32* (2006.01)

(52) U.S. Cl.
CPC .......... *A61K 9/7069* (2013.01); *A61K 9/7084* (2013.01); *A61K 31/27* (2013.01); *A61K 31/4748* (2013.01); *A61K 47/14* (2013.01); *A61K 47/32* (2013.01); *A61F 2013/0296* (2013.01)

(56) References Cited

U.S. PATENT DOCUMENTS

| | | | | |
|---|---|---|---|---|
| 2015/0030666 A1* | 1/2015 | Ogino | ............... | A61K 9/7053 514/648 |
| 2015/0112285 A1* | 4/2015 | Prinz | ............... | A61K 9/7084 604/290 |
| 2016/0317465 A1* | 11/2016 | Shinoda | ............... | A61K 31/325 |

FOREIGN PATENT DOCUMENTS

| | | | |
|---|---|---|---|
| EP | 3228309 | A1 | 10/2017 |
| EP | 2752188 | B1 | 5/2020 |
| JP | 2011518776 | A | 6/2011 |
| JP | 2016130264 | A | 7/2016 |
| TW | 201713316 | A | 4/2017 |
| WO | WO-2007145996 | A2 | 12/2007 |
| WO | WO-2009120277 | A1 * 10/2009 ........... A61K 31/166 |
| WO | WO-2010124187 | A1 | 10/2010 |
| WO | WO-2015087927 | A1 | 6/2015 |
| WO | WO-2016088898 | A1 | 6/2016 |
| WO | WO-2016130408 | A1 | 8/2016 |
| WO | WO-2017006974 | A1 | 1/2017 |
| WO | WO-2018015424 | A1 | 1/2018 |

OTHER PUBLICATIONS

Sakakibara, R., et al., "How to Manage Overactive Bladder in Elderly Individuals with Dementia? A Combined Use of Donepezil, a Central Acetylcholinesterase Inhibitor, and Propiverine, a Peripheral Muscarine Receptor Antagonist," *Journal of the American Geriatrics Society* 57(8): 1515-1517, Blackwell Science, United States (Aug. 2009).

Sakakibara, R., et al., "Pathophysiology of Bladder Dysfunction in Parkinson's Disease," *Neurobiology of Disease* 46(3): 565-571, Academic Press, United States (Jun. 2012).

* cited by examiner

TRANSDERMAL THERAPEUTIC SYSTEM FOR THE TRANSDERMAL ADMINISTRATION OF SOLIFENACIN

TECHNICAL FIELD OF THE INVENTION

The present invention relates to a transdermal therapeutic system (TTS) for the transdermal administration of solifenacin, processes of manufacture and uses thereof, and methods of treatments therewith.

BACKGROUND OF THE INVENTION

The active ingredient solifenacin, (1S,3'R)-1-azabicyclo[2.2.2]oct-8-yl-1-phenyl-3,4-dihydro-1H-isochinolin-2-carboxylate ($C_{23}H_{26}N_2O_2$, CAS No. 242478-37-1), is a competitive muscarinic receptor antagonist. Muscarinic receptors play an important role in several major cholinergically mediated functions, including contractions of urinary bladder smooth muscle and stimulation of salivary secretion.

Solifenacin-containing products are commercially available for oral administration. VESIcare® tablet, indicated for the treatment of overactive bladder with symptoms of urge urinary incontinence, urgency, and urinary frequency, contains 5 mg or 10 mg solifenacin succinate for once daily administration. However, for persons in need of care such as bedridden patients, dementia patients or patients who have difficulty in swallowing, such as elderly people, the oral administration is difficult. Additionally, daily administration places a large burden on the patient.

Transdermal therapeutic systems (TTS) for the transdermal administration of active agents have several advantages over other application systems. In comparison to oral dosage forms, for example, fewer side effects are observed. Furthermore, due to the simple mode of application, more convenience is accomplished for the patient. In particular, longer administration periods on the skin of human patients are beneficial for the compliance. However, it is technically challenging to provide TTS with sufficient permeation rates of the active agent for time periods as needed and with the desired physical properties and the desired wear properties.

Reports relating to substances that enhance the transdermal permeability of active agents are known, however, such transdermal permeation enhancer may also negatively affect the release profile of the active agent, for example, in that the release is too fast at the beginning of the dosing period and provide for a failure of the system for longer dosing periods. Commonly used transdermal permeation enhancer may also slow down the release of the active agent due to physical or chemical transformations of the active agent and may negatively affect the physical properties (e.g. adhesiveness, cold flow properties) of the TTS and may cause skin irritation.

There is a need in the art for a TTS for the transdermal administration of solifenacin that does not has the above mentioned problems. In particular, a need exists for a TTS for the transdermal administration of solifenacin, which provides a continuous delivery of solifenacin over an extended period of time, and is particularly suitable for a multi day therapy with a single application, thereby improving patient compliance.

OBJECTS AND SUMMARY OF THE INVENTION

It is an object of certain embodiments of the present invention to provide a TTS for the transdermal administration of solifenacin (e.g., solifenacin base).

It is a further object of certain embodiments of the present invention to provide a TTS for the transdermal administration of solifenacin (e.g., solifenacin base) that provides a permeation rate which is sufficient for achieving a therapeutically effective dose.

It is a further object of the present invention to provide a TTS for the transdermal administration of solifenacin (e.g., solifenacin base) with a high active-agent utilization, i.e. a TTS, which does not require a high excess amount of active agent in order to provide a sufficient release performance during an administration period.

It is an object of certain embodiments of the present invention to provide a TTS for the transdermal administration of solifenacin (e.g., solifenacin base), which requires a relatively small amount of solifenacin contained therein and provides a sufficient permeation rate of solifenacin over the administration period (e.g., over 24 hours or 72 hours).

It is a further object of the present invention to provide a TTS for the transdermal administration of solifenacin (e.g., solifenacin base), which requires a relatively small area of release and provides a sufficient permeation rate of solifenacin over the administration period (e.g., over 24 hours or 72 hours).

It is a further object of the present invention to provide a TTS for the transdermal administration of solifenacin (e.g., solifenacin base) that provides a permeation rate which is sufficient for reducing peripheral side effects induced by a second active agent (e.g., rivastigmine base), which is administered concomitantly.

It is an object of certain embodiments of the present invention to provide a TTS for the transdermal administration of solifenacin that is easy to manufacture.

These objects and others are accomplished by the present invention which according to one aspect relates to a transdermal therapeutic system for the transdermal administration of solifenacin comprising a solifenacin-containing layer structure, the solifenacin-containing layer structure comprises a backing layer and a solifenacin-containing layer comprising a therapeutically effective amount of solifenacin, wherein the solifenacin-containing layer structure comprises at least one polymer, and wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

It has been found that the solifenacin (e.g. solifenacin base)-containing TTS according to the present invention, which does not contain a transdermal permeation enhancer selected from the group consisting of a fatty acid ester, a terpene, and a carboxylic acid having 2 to 10 carbon atoms provides advantageous properties in terms of the continuous solifenacin delivery, the release performance and the active agent utilization. In particular, the TTS according to the present invention provides the advantageous properties over an extended period of time (e.g., at least 24 hours).

According to further aspects, the TTS according to the invention is for use in a method of treatment, preferably for use in a method of treating overactive bladder with symptoms of urge urinary incontinence, urgency, and urinary frequency.

According to further aspects, the invention relates to the use of a TTS according to the invention for the manufacture of a medicament, preferably for the manufacture of a medicament for treating overactive bladder with symptoms of urge urinary incontinence, urgency, and urinary frequency.

According to further aspects, the invention relates to a method of treatment, preferably a method of treating overactive bladder with symptoms of urge urinary incontinence, urgency, and urinary frequency, by applying to the skin of a patient a TTS according to the invention.

According to a further aspect, the invention relates to a method of reducing the peripheral side effects induced by rivastigmine by applying to the skin of a patient a transdermal therapeutic system according to the invention, preferably for at least of about 24 hours, for more than 24 hours, for at least or about 48 hours, for at least or about 72 hours, or for about 84 hours.

According to yet another aspect, the invention relates to a method of manufacture of a TTS according to the invention comprising the steps of:
1) providing a solifenacin-containing coating composition comprising
   a) solifenacin and optionally an additional active agent,
   b) optionally a solvent,
2) coating the solifenacin-containing coating composition onto a release liner in an amount to provide the desired area weight,
3) drying the coated solifenacin-containing coating composition to provide the solifenacin-containing layer,
4) laminating the solifenacin-containing layer to a backing layer to provide an solifenacin-containing layer structure,
5) optionally providing an additional skin contact layer by coating and drying an active agent-free coating composition or an active agent-containing coating composition according to steps 2 and 3, removing the release liner of the solifenacin-containing layer and laminating the adhesive side of the skin contact layer onto the adhesive side of the solifenacin-containing layer to provide an solifenacin-containing layer structure,
6) punching the individual systems from the solifenacin-containing layer structure,
7) optionally adhering to the individual systems an active agent-free self-adhesive layer structure comprising also a backing layer and an active agent-free pressure-sensitive adhesive layer and which is larger than the individual systems of the solifenacin-containing layer structure, wherein at least one polymer is added to the solifenacin-containing coating composition in step 1, or, if an additional skin contact layer is provided, to the coating composition in step 5, or to both the solifenacin-containing coating composition in step 1 and to the coating composition in step 5.

According to a specific aspect, the invention relates to a transdermal therapeutic system for the transdermal administration of solifenacin comprising a solifenacin-containing layer structure, the solifenacin-containing layer structure comprising: A) a backing layer, and B) a solifenacin-containing layer; wherein the solifenacin-containing layer comprises a) a therapeutically effective amount of solifenacin, and b) at least one polymer selected from the group consisting of a silicone pressure-sensitive adhesive and a silicone acrylic hybrid pressure-sensitive adhesive in an amount of from about 20% to about 99% by weight based on the solifenacin-containing layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

According to a specific aspect, the invention relates to a transdermal therapeutic system for the transdermal administration of solifenacin comprising a solifenacin-containing layer structure, the solifenacin-containing layer structure comprising: A) a backing layer, and B) a solifenacin-containing matrix layer; wherein the solifenacin-containing matrix layer comprises a) a therapeutically effective amount of solifenacin, and b) at least one polymer selected from the group consisting of a polymer based on polysiloxanes and a silicone acrylic hybrid polymer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

According to a specific aspect, the invention relates to a transdermal therapeutic system for the transdermal administration of solifenacin comprising a solifenacin-containing layer structure, the solifenacin-containing layer structure comprising: A) a backing layer, and B) a solifenacin-containing matrix layer; wherein the solifenacin-containing matrix layer comprises a) a therapeutically effective amount of solifenacin, and b) at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

According to another specific aspect, the invention relates to a transdermal therapeutic system for the transdermal administration of solifenacin comprising a solifenacin-containing layer structure, the solifenacin-containing layer structure comprising: A) a backing layer, B) a solifenacin-containing layer, wherein the solifenacin-containing layer comprises a) a therapeutically effective amount of solifenacin, b) at least one acrylate polymer, and c) optionally an additional active agent, C) a skin contact layer comprising at least one polymer selected from the group consisting of a silicone pressure-sensitive adhesive and a silicone acrylic hybrid pressure-sensitive adhesive in an amount of from about 20% to about 100% by weight based on the solifenacin-containing layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

According to yet another specific aspect, the invention relates to a transdermal therapeutic system for the transdermal administration of solifenacin comprising a solifenacin-containing layer structure, the solifenacin-containing layer structure comprising: A) a backing layer, B) a solifenacin-containing layer, wherein the solifenacin-containing layer comprises a) a therapeutically effective amount of solifenacin, b) at least one polymer selected from the group consisting of a polymer based on polysiloxanes, a silicone acrylic hybrid polymer, a polymer based on polyisobutylenes, a styrene-isoprene-styrene block copolymer, and an acrylate polymer, and c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof, C) optionally a skin contact layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

Definitions

Within the meaning of this invention, the term "transdermal therapeutic system" (TTS) refers to a system by which the active agent (e.g. solifenacin) is administered to the systemic circulation via transdermal delivery and refers to the entire individual dosing unit that is applied, after removing an optionally present release liner, to the skin of a patient, and which comprises a therapeutically effective amount of active agent in an active agent-containing layer structure and optionally an additional adhesive overlay on top of the active agent-containing layer structure. The active agent-containing layer structure may be located on a release liner (a detachable protective layer), thus, the TTS may further comprise a release liner. Within the meaning of this invention, the term "TTS" in particular refers to systems providing transdermal delivery, excluding active delivery for example via iontophoresis or microporation. Transdermal therapeutic systems may also be referred to as transdermal drug delivery systems (TDDS) or transdermal delivery systems (TDS).

Within the meaning of this invention, the term "solifenacin-containing layer structure" refers to the layer structure containing a therapeutically effective amount of solifenacin and comprises a backing layer and at least one active agent-containing layer. Preferably, the solifenacin-containing layer structure is a solifenacin-containing self-adhesive layer structure.

Within the meaning of this invention, the term "therapeutically effective amount" refers to a quantity of active agent in the TTS which is, if administered by the TTS to a patient, sufficient to provide a treatment of overactive bladder with symptoms of urge urinary incontinence, urgency, and urinary frequency. A TTS usually contains more active in the system than is in fact provided to the skin and the systemic circulation. This excess amount of active agent is usually necessary to provide enough driving force for the delivery from the TTS to the systemic circulation.

Within the meaning of this invention, the terms "active", "active agent", and the like, as well as the term "solifenacin" refer to solifenacin in any pharmaceutically acceptable chemical and morphological form and physical state. These forms include without limitation solifenacin in its free base form, protonated or partially protonated solifenacin, solifenacin salts, and in particular acid addition salts formed by addition of an inorganic or organic acid such as solifenacin hydrochloride or solifenacin sulphate, phosphate, tartrate, maleinate, oxalate, acetate, lactate, solvates, hydrates, clathrates, complexes and so on, as well as solifenacin in the form of particles which may be micronized, crystalline and/or amorphous, and any mixtures of the aforementioned forms. The solifenacin, where contained in a medium such as a solvent, may be dissolved or dispersed or in part dissolved and in part dispersed. In the present invention, solifenacin base is preferably dissolved or dispersed in the solvent of a polymer to form a solifenacin-containing coating composition and is contained in the dried matrix layer in dissolved or dispersed form, or in part dissolved and in part dispersed form. The terms "additional active agent" and "second active agent" are to be understood as an active agent different from solifenacin, which is administered concomitantly with solifenacin. According to certain embodiments of the present invention, an additional active agent (e.g. rivastigmine) is included in the TTS in addition to solifenacin.

When solifenacin is mentioned to be used in a particular form in the manufacture of the TTS, this does not exclude interactions between this form of solifenacin and other ingredients of the solifenacin-containing layer structure, e.g. salt formation or complexation, in the final TTS. This means that, even if solifenacin is included in its free base form, it may be present in the final TTS in protonated or partially protonated form or in the form of an acid addition salt, or, if it is included in the form of a salt, parts of it may be present as free base in the final TTS. Unless otherwise indicated, in particular the amount of solifenacin in the layer structure relates to the amount of solifenacin included in the TTS during manufacture of the TTS and is calculated based on solifenacin in the form of the free base. E.g., when a) 0.1 mmol (equal to 36.25 mg) solifenacin base or b) 0.1 mmol (equal to 48.55 mg) solifenacin succinate is included in the TTS during manufacture, the amount of solifenacin in the layer structure is, within the meaning of the invention, in both cases 36.25 mg, i.e. 0.1 mmol.

The solifenacin starting material included in the TTS during manufacture of the TTS may be in the form of particles. Solifeancin may e.g. be present in the active agent-containing layer structure in the form of particles, which are preferably homogeneously dispersed within the active agent-containing layer structure.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. solifenacin) is not dissolved or not completely dissolved. Dispersing in the sense of the invention comprises the dissolution of a part of the starting material (e.g. solifenacin particles), depending on the solubility of the starting material (e.g. the solubility of solifenacin in the coating composition).

There are two main types of TTS for active agent delivery, i.e. matrix-type TTS and reservoir-type TTS. The release of the active agent in a matrix-type TTS is mainly controlled by the matrix including the active agent itself. In contrast thereto, a reservoir-type TTS typically needs a rate-controlling membrane controlling the release of the active agent. In principle, also a matrix-type TTS may contain a rate-controlling membrane. However, matrix-type TTS are advantageous in that, compared to reservoir-type TTS, usually no rate determining membranes are necessary and no dose dumping can occur due to membrane rupture. In summary, matrix-type transdermal therapeutic systems (TTS) are less complex in manufacture and easy and convenient to use by patients.

Within the meaning of this invention, "matrix-type TTS" refers to a system or structure wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. Preferably, the matrix layer has sufficient cohesion to be self-supporting so that no sealing between other layers is required. Accordingly, the active agent-containing layer may in one embodiment of the invention be an active agent-containing matrix layer, wherein the active agent is homogeneously distributed within a polymer matrix. In certain embodiments, the active agent-containing matrix layer may comprise two active agent-containing matrix layers, which may be laminated together. Matrix-type TTS may in particular be in the form of a "drug-in-adhesive"-type TTS referring to a system wherein the active is homogeneously dissolved and/or dispersed within a pressure-sensitive adhesive matrix. In this connection, the active agent-containing matrix layer may also be referred to as active agent-containing pressure sensitive adhesive layer or active agent-containing pressure sensitive adhesive matrix layer. A TTS comprising the active agent dissolved and/or dispersed within a polymeric gel, e.g. a hydrogel, is also considered to be of matrix-type in accordance with present invention.

TTS with a liquid active agent-containing reservoir are referred to by the term "reservoir-type TTS". In such a system, the release of the active agent is preferably controlled by a rate-controlling membrane. In particular, the reservoir is sealed between the backing layer and the rate-controlling membrane. Accordingly, the active agent-containing layer may in one embodiment be an active agent-containing reservoir layer, which preferably comprises a liquid reservoir comprising the active agent. Furthermore, the reservoir-type TTS typically additionally comprises a skin contact layer, wherein the reservoir layer and the skin contact layer may be separated by the rate-controlling membrane. In the reservoir layer, the active agent is preferably dissolved in a solvent such as ethanol or water or in silicone oil. The skin contact layer typically has adhesive properties.

Reservoir-type TTS are not to be understood as being of matrix-type within the meaning of the invention. However, microreservoir TTS (biphasic systems having deposits (e.g. spheres, droplets) of an inner active-containing phase dispersed in an outer polymer phase), considered in the art to be a mixed from of a matrix-type TTS and a reservoir-type TTS that differ from a homogeneous single phase matrix-type TTS and a reservoir-type TTS in the concept of drug transport and drug delivery, are considered to be of matrix-type within the meaning of the invention. The sizes of microreservoir droplets can be determined by an optical microscopic measurement (for example by Leica MZ16 including a camera, for example Leica DSC320) by taking pictures of the microreservoirs at different positions at an enhancement factor between 10 and 400 times, depending on the required limit of detection. By using imaging analysis software, the sizes of the microreservoirs can be determined.

Within the meaning of this invention, the term "active agent-containing layer" refers to a layer containing the active agent and providing the area of release. The term covers active agent-containing matrix layers and active agent-containing reservoir layers. If the active agent-containing layer is an active agent-containing matrix layer, said layer is present in a matrix-type TTS. If the polymer is a pressure-sensitive adhesive, the matrix layer may also represent the adhesive layer of the TTS, so that no additional skin contact layer is present. Alternatively, an additional skin contact layer may be present as adhesive layer, and/or an adhesive overlay is provided. The additional skin contact layer is typically manufactured such that it is active agent-free. However, due to the concentration gradient, the active agent will migrate from the matrix layer to the additional skin contact layer over time, until equilibrium is reached. The additional skin contact layer may be present on the active agent-containing matrix layer or separated from the active agent-containing matrix layer by a membrane, preferably a rate controlling membrane. Preferably, the active agent-containing matrix layer has sufficient adhesive properties, so that no additional skin contact layer is present. If the active agent-containing layer is an active agent-containing reservoir layer, said layer is present in a reservoir-type TTS, and the layer comprises the active agent in a liquid reservoir. In addition, an additional skin contact layer is preferably present, in order to provide adhesive properties. Preferably, a rate-controlling membrane separates the reservoir layer from the additional skin contact layer. The additional skin contact layer can be manufactured such that it is active agent-free or active agent-containing. If the additional skin contact layer is free of active agent the active agent will migrate, due to the concentration gradient, from the reservoir layer to the skin contact layer over time, until equilibrium is reached. Additionally an adhesive overlay may be provided.

As used herein, the active agent-containing layer is preferably an active agent-containing matrix layer, and it is referred to the final solidified layer. Preferably, an active agent-containing matrix layer is obtained after coating and drying the solvent-containing coating composition as described herein. Alternatively an active-agent containing matrix layer is obtained after melt-coating and cooling. The active agent-containing matrix layer may also be manufactured by laminating two or more such solidified layers (e.g. dried or cooled layers) of the same composition to provide the desired area weight. The matrix layer may be self-adhesive (in the form of a pressure sensitive adhesive matrix layer), or the TTS may comprise an additional skin contact layer of a pressure sensitive adhesive for providing sufficient tack. Preferably, the matrix layer is a pressure sensitive adhesive matrix layer. Optionally, an adhesive overlay may be present. A matrix layer according to the present invention does not contain a non-volatile solvent in an amount of more than 40% by weight based on the matrix layer. In certain embodiments of the invention, the active agent-containing matrix layer contains a non-volatile solvent in an amount of from about 5% to about 20% by weight based on the active agent-containing matrix layer. Preferably, the active agent-containing matrix layer contains no non-volatile solvents.

Within the meaning of this invention, the term "pressure-sensitive adhesive" (also abbreviated as "PSA") refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix layer or in the form of an additional layer, i.e. a pressure sensitive adhesive skin contact layer. An adhesive overlay may still be employed to advance adhesion. The pressure-sensitive adhesive properties of a pressure-sensitive adhesive depend on the polymer or polymer composition used.

Within the meaning of this invention, the term "silicone acrylic hybrid polymer" refers to a polymerization product including repeating units of a silicone sub-species and an acrylate-sub species. The silicone acrylic hybrid polymer thus comprises a silicone phase and an acrylic phase. The term "silicone acrylic hybrid" is intended to denote more than a simple blend of a silicone-based sub-species and an acrylate-based sub-species. Instead, the term denotes a polymerized hybrid species that includes silicone-based sub-species and acrylate-based sub-species that have been polymerized together. The silicone acrylic hybrid polymer may also be referred to as a "silicone acrylate hybrid polymer" as the terms acrylate and acrylic are generally used interchangeably in the context of the hybrid polymers used in the present invention.

Within the meaning of this invention, the term "silicone acrylic hybrid pressure-sensitive adhesive" refers to a silicone acrylic hybrid polymer in the form of a pressure-sensitive adhesive. Silicone acrylic hybrid pressure-sensitive adhesives are described, for example, in EP 2 599 847 and WO 2016/130408. Examples of silicone acrylic hybrid pressure-sensitive adhesives include the PSA series 7-6100 and 7-6300 manufactured and supplied in n-heptane or ethyl acetate by Dow Corning (7-610X and 7-630X; X=1 n-heptane-based/X=2 ethyl acetate-based). It was found that, depending on the solvent in which the silicone acrylic hybrid PSA is supplied, the arrangement of the silicone phase and the acrylic phase providing a silicone or acrylic continuous external phase and a corresponding discontinuous internal phase is different. If the silicone acrylic hybrid PSA is supplied in n-heptane, the composition contains a continuous, silicone external phase and a discontinuous, acrylic internal phase. If the silicone acrylic hybrid PSA composition is supplied in ethyl acetate, the composition contains a continuous, acrylic external phase and a discontinuous, silicone internal phase.

Within the meaning of this invention, the term "silicon-containing pressure-sensitive adhesive composition comprising acrylate or methacrylate functionality" comprises the condensation reaction product of a silicone resin, a silicone polymer, and a silicon-containing capping agent which provides said acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

As used herein, an active agent-containing matrix layer is a layer containing the active agent dissolved or dispersed in at least one polymer, or containing the active agent dissolved in a solvent to form an active agent-solvent mixture that is dispersed in the form of deposits (in particular droplets) in at least one polymer. Preferably, the at least one polymer is a polymer-based pressure-sensitive adhesive (e.g. a silicone pressure-sensitive adhesive or a silicone acrylic hybrid pressure-sensitive adhesive). Within the meaning of this invention, the term "pressure-sensitive adhesive layer" refers to a pressure-sensitive adhesive layer obtained from a solvent-containing adhesive coating composition after coating on a film and evaporating the solvents.

Within the meaning of this invention, the term "skin contact layer" refers to the layer included in the active agent-containing layer structure to be in direct contact with the skin of the patient during administration. This may be the active agent-containing layer. When the TTS comprises an additional skin contact layer, the other layers of the active agent-containing layer structure do not contact the skin and do not necessarily have self-adhesive properties. As outlined above, an additional skin contact layer attached to the active agent-containing layer may over time absorb parts of the active agent. An additional skin contact layer may be used to enhance adherence. The sizes of an additional skin contact layer and the active agent-containing layer are usually coextensive and correspond to the area of release. However, the area of the additional skin contact layer may also be greater than the area of the active agent-containing layer. In such a case, the area of release still refers to the area of the active agent-containing layer.

Within the meaning of this invention, the term "area weight" refers to the dry weight of a specific layer, e.g. of the matrix layer, provided in $g/m^2$. The area weight values are subject to a tolerance of ±10%, preferably ±7.5%, due to manufacturing variability.

If not indicated otherwise "%" refers to % by weight.

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2000, preferably above 5000 and more preferably above 10,000 Dalton. Correspondingly, compounds with a molecular weight below 2000, preferably below 5000 or more preferably below 10,000 Dalton are usually referred to as oligomers.

Within the meaning of this invention, the term "cross-linking agent" refers to a substance which is able to cross-link functional groups contained within the polymer.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer that may provide occlusive or non-occlusive properties and an adhesive layer. Preferably, the backing layer of the adhesive overlay provides non-occlusive properties.

Within the meaning of this invention, the term "backing layer" refers to a layer which supports the active agent-containing layer or forms the backing of the adhesive overlay. At least one backing layer in the TTS and usually the backing layer of the active agent-containing layer is substantially impermeable to the active agent contained in the layer during the period of storage and administration and thus prevents active loss or cross-contamination in accordance with regulatory requirements. Preferably, the backing layer is also occlusive, meaning substantially impermeable to water and water-vapor. Suitable materials for a backing layer include polyethylene terephthalate (PET), polyethylene (PE), ethylene vinyl acetate-copolymer (EVA), polyurethanes, and mixtures thereof. Suitable backing layers are thus for example PET laminates, EVA-PET laminates and PE-PET laminates. Also suitable are woven or non-woven backing materials.

The TTS according to the present invention can be characterized by certain parameters as measured in an in vitro skin permeation test.

Where not otherwise indicated, the in vitro permeation test is performed with dermatomed split-thickness human skin with a thickness of 500 μm and an intact epidermis, and with phosphate buffer pH 5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in g/cm$^2$ and relates to the amount of active permeated in a sample interval at certain elapsed time. E.g., in an in vitro permeation test as described above, wherein the amount of active permeated into the receptor medium has been e.g. measured at hours 0, 8, 24, 32, 48 and 72, the "permeated amount" of active can be given e.g. for the sample interval from hour 32 to hour 48 and corresponds to the measurement at hour 48, wherein the receptor medium has been exchanged completely at hour 32.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 8, 24, 32, 48 and 72, the "cumulative permeated amount" of active at hour 48 corresponds to the sum of the permeated amounts from hour 0 to hour 8, hour 8 to hour 24, hour 24 to hour 32, and hour 32 to hour 48.

Within the meaning of this invention, the parameter "skin permeation rate" for a certain sample interval at certain elapsed time is provided in g/cm$^2$-hr and is calculated from the permeated amount in said sample interval as measured by in vitro permeation test as described above in g/cm$^2$, divided by the hours of said sample interval. E.g. the skin permeation rate in an in vitro permeation test as described above, wherein the amount of active permeated into the receptor medium has been e.g. measured at hours 0, 8, 24, 32, 48 and 72, the "skin permeation rate" at hour 48 is calculated as the permeated amount in the sample interval from hour 32 to hour 48 divided by 16 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 8, 24, 32, 48 and 72, the "cumulative skin permeation rate" at hour 48 is calculated as the cumulative permeated amount at hour 48 (see above) divided by 48 hours, unless indicated otherwise.

Within the meaning of this invention, the ter "release performance" refers to the parameters which express the release of the active agent per cm$^2$, such as the "permeated amount", the "cumulative permeated amount", the "skin permeation rate" and the "cumulative skin permeation rate".

Within the meaning of this invention, the term "active agent utilization" refers to the cumulative permeated amount after a certain elapsed time, e.g. after 72 hours, divided by the initial loading of the active agent, and can be presented in % by multiplying with 100.

Within the meaning of this invention, the above parameters "permeated amount" and "skin permeation rate" (as well as "cumulative permeated amount" and "cumulative skin permeation rate") refer to mean values calculated from at least 3 in vitro permeation test experiments. Where not otherwise indicated, the standard deviation (SD) of these mean values refer to a corrected sample standard deviation, calculated using the formula:

$$SD = \sqrt{\frac{1}{n-1}\sum_{i=1}^{n}(x_i - \bar{x})^2}$$

wherein n is the sample size, $\{x_1, x_2, \ldots x_n\}$ are the observed values and x is the mean value of the observed values.

The TTS according to the present invention can also be characterized by certain parameters as measured in an in vivo clinical study.

Within the meaning of this invention, the parameter "mean release rate" refers to the mean release rate in μg/hr or in mg/day over the period of administration (e.g., 1 to 7 days) by which the active agent is released through the human skin into the systemic circulation and is based on the AUC obtained over said period of administration in a clinical study.

Within the meaning of this invention, the term "extended period of time" relates to a period of at least or about 24 hours (1 day), at least or about 48 hours (2 days), at least or about 72 hours (3 days), or about 84 hours (3.5 days).

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention, the term "coating composition" refers to a composition comprising all components of the matrix layer in a solvent, which may be coated onto the backing layer or release liner to form the matrix layer upon drying. 10067 Within the meaning of this invention, the term "pressure sensitive adhesive composition" refers to a pressure sensitive adhesive at least in mixture with a solvent (e.g. n-heptane or ethyl acetate).

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, toluene and mixtures thereof.

DETAILED DESCRIPTION

TTS Structure

Figure 1A:
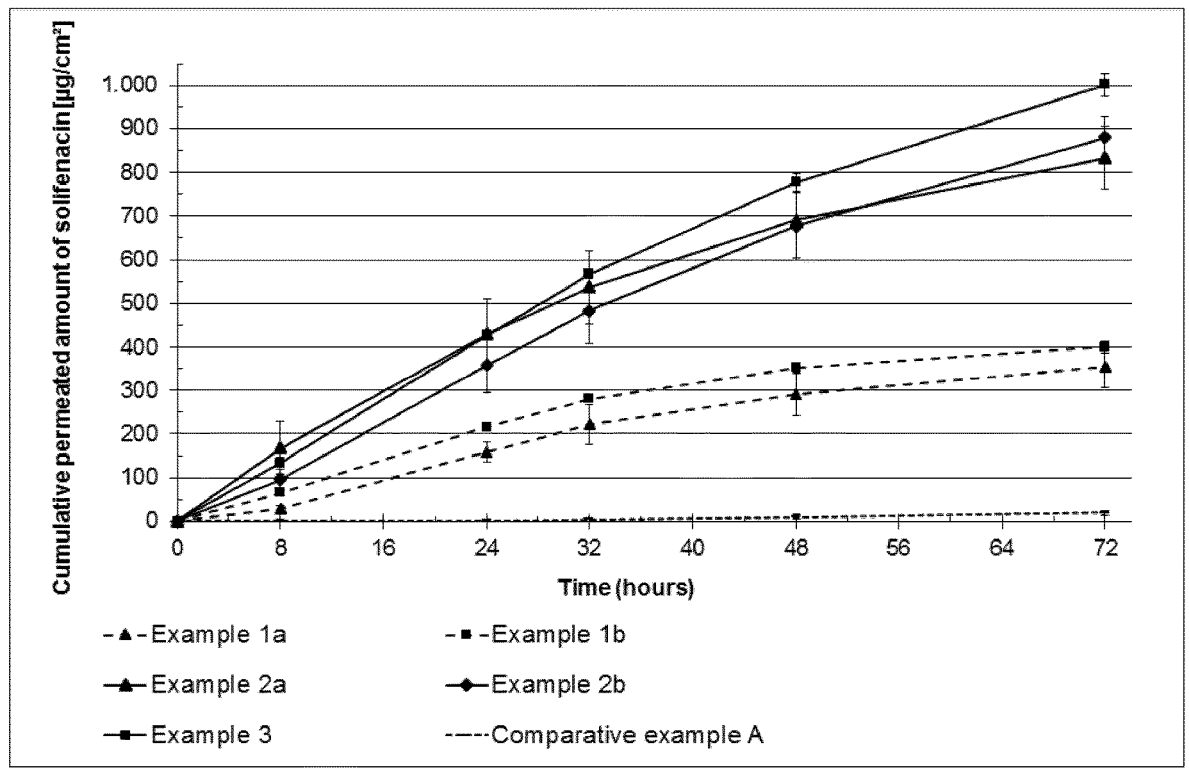
FIG. 1a depicts the cumulative permeated amount of solifenacin of Example 1a, Example 1b, Example 2a, Example 2b, Example 3 and Comparative example A over a time interval of 72 hours.
Figure 1B:
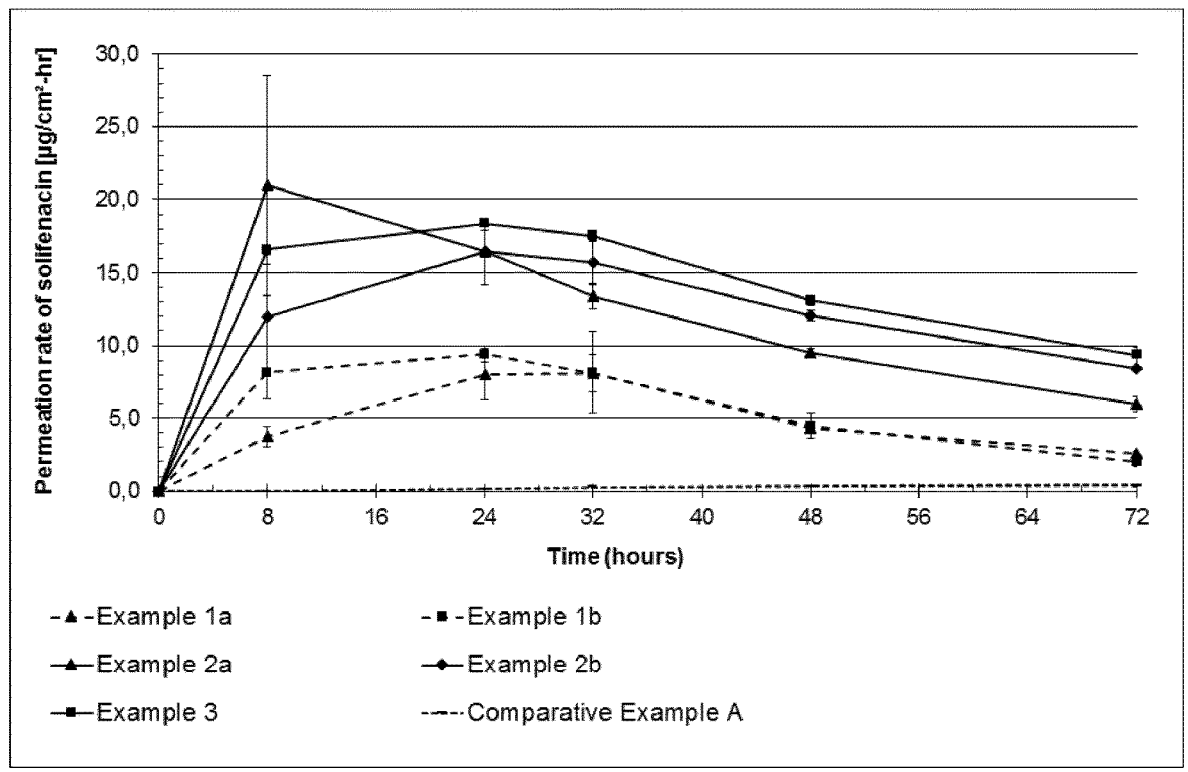
FIG. 1b depicts the skin permeation rate of Example 1a, Example 1b, Example 2a, Example 2b, Example 3 and Comparative example A over a time interval of 72 hours.
Figure 2A:
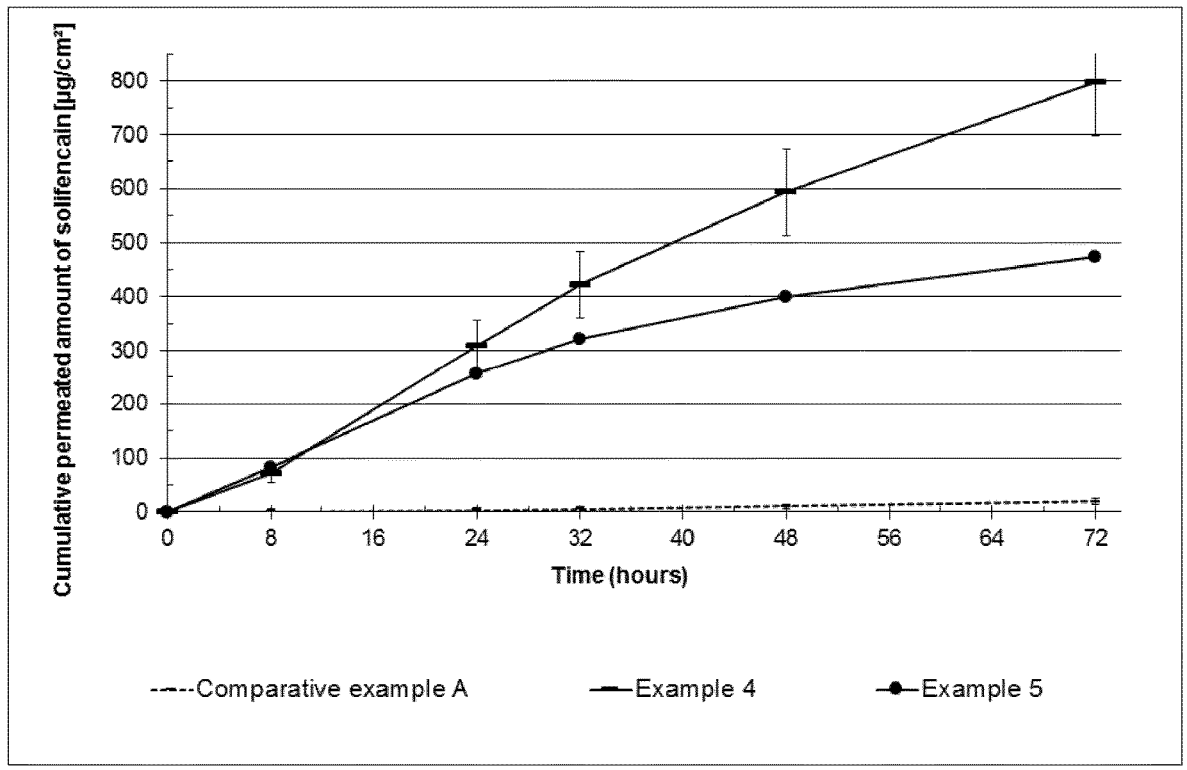
FIG. 2a depicts the cumulative permeated amount of solifenacin of Example 4, Example and Comparative example A over a time interval of 72 hours.
Figure 2B:
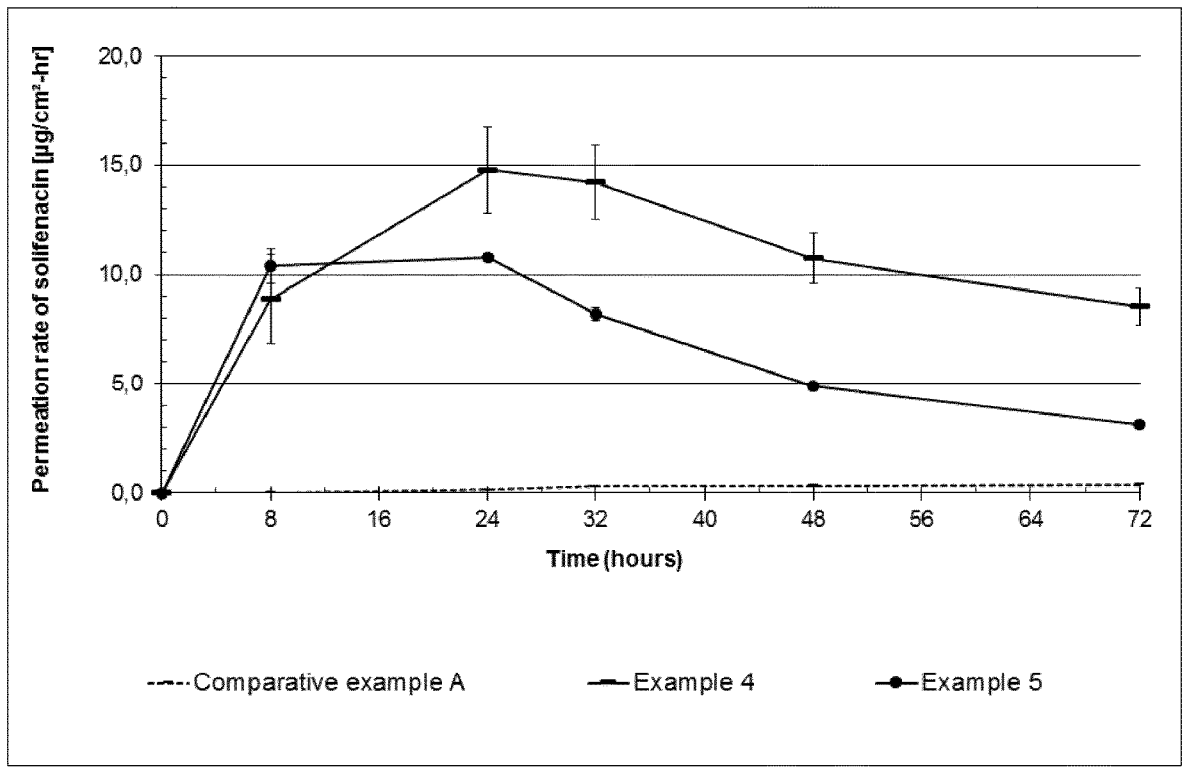
FIG. 2b depicts the skin permeation rate of Example 4, Example 5 and Comparative example A over a time interval of 72 hours.

The present invention relates to a transdermal therapeutic system for the transdermal administration of solifenacin comprising a solifenacin-containing layer structure.

The solifenacin-containing layer structure according to the invention comprises A) a backing layer and B) a solifenacin-containing layer comprising a therapeutically effective amount of solifenacin. The solifenacin-containing layer structure is preferably a solifenacin-containing self-adhesive layer structure.

According to the present invention, the solifenacin-containing layer structure also comprises at least one polymer.

Thus, in a first aspect, the present invention relates to a transdermal therapeutic system for the transdermal administration of solifenacin comprising a solifenacin-containing layer structure,
the solifenacin-containing layer structure comprising:
A) a backing layer; and
B) a solifenacin-containing layer comprising a therapeutically effective amount of solifenacin,
wherein solifenacin-containing layer structure comprises at least one polymer.

The transdermal therapeutic system according to the invention does not contain a transdermal permeation enhancer selected from the group consisting of a fatty acid ester, a terpene, and a carboxylic acid having 2 to 10 carbon atoms, in particular, the transdermal therapeutic system according to the invention does not contain a fatty acid ester, a terpene, and a carboxylic acid having 2 to 10 carbon atoms.

Preferably, the transdermal therapeutic system according to the invention does not contain a transdermal permeation enhancer selected from the group consisting a fatty acid ester, a terpene, and a carboxylic acid, in particular, the transdermal therapeutic system according to the invention does not contain a fatty acid ester, a terpene, and a carboxylic acid. More preferably, the transdermal therapeutic system according to the invention does not contain a transdermal permeation enhancer.

The at least one polymer is preferably selected from the group consisting of a polymer based on polysiloxanes, a silicone acrylic hybrid polymer, a polymer based on polyisobutylenes, a styrene-isoprene-styrene block copolymer, and an acrylate polymer, more preferably from the group consisting of a polymer based on polysiloxanes, a silicone acrylic hybrid polymer, a polymer based on polyisobutylenes, and an acrylate polymer, in particular preferred from the group consisting of a polymer based on polysiloxanes and a silicone acrylic hybrid polymer. In certain embodiments, the solifenacin-containing layer structure comprises at least one polymer based on polysiloxanes. In certain embodiments, the solifenacin-containing layer structure comprises at least one silicone acrylic hybrid polymer. In certain embodiments, the solifenacin-containing layer structure comprises at least one polyisobutylene. In certain embodiments, the solifenacin-containing layer structure comprises at least one acrylate polymer. In certain embodiments, the solifenacin-containing layer structure comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer.

The backing layer is preferably substantially solifenacin-impermeable. Furthermore, it is preferred that the backing layer is occlusive as outlined above.

The solifenacin-containing layer may be directly attached to the backing layer, so that no further layer between the backing layer and the solifenacin-containing layer is present.

The TTS according to the present invention may be a matrix-type TTS or a reservoir-type TTS, and preferably is a matrix-type TTS.

The solifenacin-containing layer structure according to the invention is normally located on a detachable protective layer (release liner), from which it is removed immediately before application to the surface of the patient's skin. Thus, the TTS may further comprise a release liner. A TTS protected this way is usually stored in a blister pack or a seam-sealed pouch. The packaging may be child resistant and/or senior friendly.

In one embodiment of the present invention, the solifenacin-containing layer is a solifenacin-containing pressure sensitive adhesive layer and represents the skin contact layer. That is, the solifenacin-containing layer structure does not comprise an additional skin contact layer attached to the solifenacin-containing layer. In this connection, the solifenacin-containing layer comprises the at least one polymer (e.g. a silicone acrylic hybrid polymer or a non-hybrid polymer e.g. based on polysiloxanes) and is preferably a solifenacin-containing matrix layer, which is self-adhesive. The self-adhesive properties of the solifenacin-containing layer structure are preferably provided by the polymer. Thus, in a preferred embodiment of the invention, the at least one polymer is a pressure sensitive adhesive. Further details regarding the at least one polymer according to the invention are provided further below.

In another embodiment of the present invention, the solifenacin-containing layer structure further comprises an additional skin contact layer. The skin contact layer is preferably self-adhesive and provides the adhesive properties.

In one embodiment of the present invention, the solifenacin-containing layer structure further comprises C) a skin contact layer on the solifenacin-containing layer, and the at least one polymer is contained in the skin contact layer. In this connection, the solifenacin-containing layer may also contain at least one polymer, which may be the same polymer as the at least one polymer contained in the solifenacin-containing layer or a different polymer. For example, when the additional skin contact layer comprises a pressure-sensitive adhesive based on polysiloxanes, the solifenacin-containing layer may comprises the same pressure-sensitive adhesive based on polysiloxanes, or a different pressure-sensitive adhesive based on polysiloxanes or a different non-hybrid polymer or a hybrid polymer.

In one embodiment of the present invention, the solifenacin-containing layer structure comprises an additional skin contact layer on the solifenacin-containing layer, and the at least one polymer (e.g. a polymer based on polysiloxanes or a silicone acrylic hybrid polymer) is contained in both the solifenacin-containing layer and the skin contact layer.

In one embodiment of the present invention, the solifenacin-containing layer structure comprises an additional active agent. The additional active agent may be any additional active agent reasonable for an administration together with solifenacin. The additional active agent (e.g. rivastigmine) may be contained in the solifenacin-containing layer or in an additional layer. The additional active agent is preferably contained in a therapeutically effective amount.

In one embodiment of the present invention, the solifenacin-containing layer structure comprises:
A) a backing layer,
B) a solifenacin-containing layer comprising
 a) a therapeutically effective amount of solifenacin, and
 b) a therapeutically effective amount of an additional active agent (e.g. rivastigmine), and
C) a skin contact layer comprising at least one polymer.

In one embodiment of the present invention, the solifenacin-containing layer structure further comprises rivastigmine in addition to the solifenacin. In this connection, it is believed that the TTS according to the present invention can reduce peripheral side effects induced by rivastigmine. Thereby, the efficacy and the daily dose of rivastigmine can be increased.

In one embodiment of the present invention, an at least one additional layer may be between the solifenacin-containing layer and the additional skin contact layer. It is however preferred that the additional skin contact layer is attached to the solifenacin-containing layer.

According to certain embodiments of the invention, the TTS may further comprise an adhesive overlay. This adhesive overlay is in particular larger in area than the solifenacin-containing structure and is attached thereto for enhancing the adhesive properties of the overall transdermal therapeutic system. Said adhesive overlay comprises a backing layer and an adhesive layer. The adhesive overlay provides additional area adhering to the skin but does not add to the area of release of the solifenacin. The adhesive overlay comprises a self-adhesive polymer or a self-adhesive polymer mixture selected from the group consisting of silicone acrylic hybrid polymers, acrylic polymers, polysiloxanes, polyisobutylenes, styrene-isoprene-styrene copolymers, and mixtures thereof, which may be identical to or different from any polymer or polymer mixture included in the solifenacin-containing layer structure. In one embodiment, the TTS is free of an adhesive overlay on top of the solifenacin-containing layer structure.

Depending on the dosage, the area of release of the TTS ranges from about 1 $cm^2$ to about 50 $cm^2$, preferably from about 1 $cm^2$ to less than 50 $cm^2$.

In one particular embodiment, the invention relates to a transdermal therapeutic system for the transdermal administration of solifenacin comprising a solifenacin-containing layer structure, the solifenacin-containing layer structure comprising: A) a backing layer; and B) a solifenacin-containing layer; wherein the solifenacin-containing layer comprises a) a therapeutically effective amount of solifenacin, and b) at least one polymer selected from the group consisting of a silicone pressure-sensitive adhesive and a silicone acrylic hybrid pressure-sensitive adhesive in an amount of from about 20% to about 99% by weight based on the solifenacin-containing layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

In one particular embodiment, the solifenacin-containing layer structure comprises A) a backing layer, and B) a solifenacin-containing matrix layer; wherein the solifenacin-containing matrix layer comprises a) a therapeutically effective amount of solifenacin, and b) at least one polymer selected from the group consisting of a polymer based on polysiloxanes and a silicone acrylic hybrid polymer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

In another particular embodiment, the solifenacin-containing layer structure comprises A) a backing layer, and B) a solifenacin-containing matrix layer; wherein the solifenacin-containing matrix layer comprises a) a therapeutically effective amount of solifenacin, and b) at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

In another particular embodiment, the invention relates to a transdermal therapeutic system for the transdermal administration of solifenacin comprising a solifenacin-containing layer structure, the solifenacin-containing layer structure comprising: A) a backing layer; and B) a solifenacin-containing layer; wherein the solifenacin-containing layer comprises a) a therapeutically amount of solifenacin, b) at least one acrylate polymer, and c) optionally an additional active agent, C) a skin contact layer comprising at least one polymer selected from the group consisting of a silicone pressure-sensitive adhesive and a silicone acrylic hybrid pressure-sensitive adhesive in an amount of from about 20% to about 100% by weight based on the solifenacin-containing layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

In yet another particular embodiment, the invention relates to a transdermal therapeutic system for the transdermal administration of solifenacin comprising a solifenacin-containing layer structure, the solifenacin-containing layer structure comprising: A) a backing layer, B) a solifenacin-containing layer, wherein the solifenacin-containing layer comprises a) a therapeutically effective amount of solifenacin, b) at least one polymer selected from the group consisting of a polymer based on polysiloxanes, a silicone acrylic hybrid polymer, a polymer based on polyisobutylenes, a styrene-isoprene-styrene block copolymer, and an acrylate polymer, and c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof, C) optionally a skin contact layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

In yet another particular embodiment, the solifenacin-containing layer structure comprises A) a backing layer, B) a solifenacin-containing layer, wherein the solifenacin-containing layer comprises a) a therapeutically effective amount of solifenacin, b) a blend of a polymer based on polysiloxanes and an acrylate polymer, and c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof, C) optionally a skin contact layer, wherein the transdermal therapeutic system does not contain a transdermal permeation enhancer selected from the group consisting of a fatty acid ester, a terpene, and a carboxylic acid having 2 to 10 carbon atoms, or wherein the transdermal therapeutic system does not contain a fatty acid ester, a terpene or a carboxylic acid having 2 to 10 carbon atoms, in particular wherein the transdermal therapeutic system does not contain a fatty acid ester, a terpene or a carboxylic acid, more particular wherein the transdermal therapeutic system does not contain a transdermal permeation enhancer.

Solifenacin-Containing Layer

As outlined in more detail above, the TTS according to the present invention comprises a solifenacin-containing layer structure comprising a solifenacin-containing layer. The solifenacin-containing layer according to the invention comprises a therapeutically effective amount of the solifenacin.

The solifenacin-containing layer may be a solifenacin-containing matrix layer or a solifenacin-containing reservoir layer. It is preferred that the solifenacin-containing layer is a solifenacin-containing matrix layer, which comprises solifenacin homogeneously dispersed or dissolved in the polymer matrix. In yet another preferred embodiment, the solifenacin-containing layer is a solifenacin-containing biphasic matrix layer, which comprises solifenacin-containing deposits homogeneously dispersed in the polymer matrix.

In one embodiment, the solifenacin-containing layer is a self-adhesive solifenacin-containing layer, more preferably a self-adhesive solifenacin-containing matrix layer.

In a certain embodiment, the solifenacin-containing layer is obtainable by coating and drying a solifenacin-containing coating composition that comprises the solifenacin in the form of the free base.

According to certain embodiments, the solifenacin-containing layer has an area weight of from about 20 to about 160 $g/m^2$, from about 40 to about 150 $g/m^2$, or from about 50 to about 140 $g/m^2$.

In a certain embodiment, the solifenacin-containing layer contains the solifenacin in an amount of from 2% to 40%, preferably from 3% to 40%, more preferably from 3% to 35% by weight based on the solifenacin-containing layer.

According to certain embodiments, the solifenacin-containing layer contains the at least one polymer. The at least one polymer is preferably selected from the group consisting of a polymer based on polysiloxanes, a silicone acrylic hybrid polymer, a polymer based on polyisobutylenes, a styrene-isoprene-styrene block copolymer, and an acrylate polymer, more preferably selected from the group consisting of a polymer based on polysiloxanes and a silicone acrylic hybrid polymer.

The at least one polymer is preferably contained in an amount of from about 20% to about 99% by weight, more preferably of from about 30% to about 99% by weight, particularly preferably of from about 40% to about 99% by weight based on the solifenacin-containing layer.

In one embodiment, the solifenacin-containing layer comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer, preferably in an amount ratio of 0.1:1 to 1:0.1, more preferably of 0.5:1 to 1:0.5, particularly preferred of 1:1.

In one preferred embodiment, the solifenacin-containing layer comprises a blend of at least two polymers based on polysiloxanes which are characterized by different physical properties, preferably in an amount ratio of 0.5:1 to 1:0.5.

In another preferred embodiment, the solifenacin-containing layer comprises a blend of a polymer based on polysiloxanes and an acrylate polymer, preferably in an amount ratio of 0.5:1 to 1:0.5.

In one particular embodiment, the solifenacin-containing layer comprises a blend of at least two silicone acrylic hybrid polymers which are characterized by different physical properties, preferably in an amount ratio of 0.5:1 to 1:0.5.

In another particular embodiment, the solifenacin-containing layer comprises a blend of a silicone acrylic hybrid polymer and a non-hybrid polymer selected from the group consisting of a polymer based on polysiloxanes, a polymer based on polyisobutylenes, a styrene-isoprene-styrene block copolymer, and an acrylate polymer. In this connection, the silicone acrylic hybrid polymer and the non-hybrid polymer may be contained in the solifenacin-containing layer in an amount ratio of from 0.1:1 to 1:0.1, and are preferably contained in an amount ratio of from 0.5:1 to 1:0.5.

Ina particular embodiment, the solifenacin-containing layer comprises a blend of a silicone acrylic hybrid polymer and a polymer based on polysiloxanes, preferably in an amount ratio of 0.5:1 to 1:0.5.

In another particular embodiment, the solifenacin-containing layer comprises a blend of a silicone acrylic hybrid polymer and an acrylate polymer, preferably in an amount ratio of 0.5:1 to 1:0.5.

In another embodiment, the solifenacin-containing layer comprises a blend of at least two polyisobutylenes which are characterized by different physical properties, preferably in an amount ratio of 0.5:1 to 1:0.5.

In certain embodiments, the solifenacin-containing layer further comprises an auxiliary polymer. The auxiliary polymer may be contained in an amount of from about 0.5% to about 20%, from about 0.5% to about 10%, or from about 1% to about 5% by weight based on the solifenacin-containing layer. The auxiliary polymer is preferably selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof. In one embodiment, the auxiliary polymer is a vinylpyrrolidone-vinyl acetate copolymer or a polyvinylpyrrolidone. In another embodiment, the auxiliary polymer is a alkyl methacrylate copolymer or a methacrylic ester copolymer.

Ina certain embodiment, the at least one polymer (e.g. a polymer based on polysiloxanes or a silicone acrylic hybrid polymer) is contained in the solifenacin-containing layer and the solifenacin-containing layer further comprises an auxiliary polymer such that the solifenacin-containing layer comprises a) a therapeutically effective amount of solifenacin,
   b) at least one polymer, preferably selected from the group consisting of a polymer based on polysiloxanes and a silicone acrylic hybrid polymer, and
   c) at least one auxiliary polymer, preferably selected from the group consisting of alkyl methacrylate copolymers, amino alkyl methacrylate copolymers, methacrylic acid copolymers, methacrylic ester copolymers, ammonio-alkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof.

According to certain embodiments, the total amount of polymer contained in the solifenacin-containing layer ranges from about 40% to about 99% by weight, preferably from about 50% to about 99% by weight, more preferably from about 60% to about 99% by weight based on the solifenacin-containing layer.

As indicated above, according to certain embodiments of the present invention, the solifenacin-containing layer contains and additional active agent (e.g. rivastigmine).

In certain embodiments, the solifenacin-containing layer is a solifenacin-containing matrix layer containing a non-volatile solvent (e.g. a fatty alcohols) in an amount of from about 5% to about 20% by weight based on the solifenacin-containing matrix layer.

In one embodiment, the solifenacin-containing layer is a solifenacin-containing biphasic matrix layer having an inner phase comprising the therapeutically effective amount of solifenacin, and having an outer phase comprising the at least one polymer, wherein the inner phase forms dispersed deposits in the outer phase. In a certain embodiment of the present invention, the content of the inner phase in the biphasic matrix layer is from about 5% to 40% by volume based on the volume of the biphasic matrix layer.

The TTS according to the invention may further comprise one or more anti-oxidants. Suitable anti-oxidants are sodium metabisulfite, ascorbyl palmitate, tocopherol and esters thereof, ascorbic acid, butylhydroxytoluene, butylhydroxyanisole or propyl gallate, preferably butylhydroxytoluene, ascorbyl palmitate and tocopherol. The anti-oxidants may be conveniently present in the solifenacin-containing layer, preferably in an amount of from about 0.001 to about 1.0% of the solifenacin-containing layer, ore preferably in an amount of from about 0.02 to about 0.5% of the solifenacin-containing layer.

The TTS according to the invention may further comprise in addition to the above mentioned ingredients at least one excipient or additive, for example from the group of cross-linking agents, solubilizers, fillers, tackifiers, film-forming agents, plasticizers, stabilizers, softeners, substances for skincare, permeation enhancers, pH regulators, and preservatives. In general, it is preferred according to the invention that no additional excipients or additives are required. Thus, the TTS has a composition of low complexity. In certain embodiments, no further additive (e.g. a transdermal permeation enhancer) is present in the TTS.

In certain embodiments, the solifenacin-containing layer comprises a transdermal permeation enhancer that is not selected from the group consisting of a fatty acid ester, a terpene, and a carboxylic acid having 2 to 20 carbon atoms. Permeation enhancers are substances, which influence the barrier properties of the stratum corneum in the sense of increasing the active agent permeability. Suitable permeation enhancer according to the invention are, for example, pentylacetate and laurylalcohol.

In one embodiment of the present invention, the solifenacin-containing layer consists of active agent (the therapeutically effective amount of solifenacin and optionally an additional active agent) and polymer.

When using an additional skin contact layer, the ingredients of the solifenacin-containing layer such as the solifenacin and optional additional active agents, optional auxiliary polymers, optional anti-oxidants, and optional additional excipients or additives may over time migrate into the additional skin contact layer. This however depends on the ingredients and the material of the skin contact layer.

Skin Contact Layer

In one embodiment of the invention, the solifenacin-containing layer represents the skin contact layer. In another embodiment of the invention, the solifenacin-containing layer structure comprises an additional skin contact layer.

In certain embodiments of the invention, wherein the solifenacin-containing layer structure comprises an additional skin contact layer, the additional skin contact layer is preferably self-adhesive. The additional skin contact layer is preferably obtainable by coating and drying an adhesive coating composition.

In certain embodiments of the invention, wherein the solifenacin-containing layer structure comprises an additional skin contact layer, the additional skin contact layer has an area weight of from about 10 to about 160 $g/m^2$, from about 10 to about 100 $g/m^2$, or from about 10 to about 60 $g/m^2$.

In certain embodiments of the invention, wherein the solifenacin-containing layer structure comprises an additional skin contact layer, the additional skin contact layer comprises the at least one polymer. The at least one polymer is preferably selected from the group consisting of a polymer based on polysiloxanes, a silicone acrylic hybrid polymer, a polymer based on polyisobutylenes, a styrene-isoprene-styrene block copolymer, and an acrylate polymer, more preferably selected from the group consisting of a polymer based on polysiloxanes and a silicone acrylic hybrid polymer. Preferably, the at least one polymer in the skin contact layer is a pressure-sensitive adhesive polymer.

According to certain embodiments, the skin contact layer contains the at least one polymer in an amount of from about 20% to about 100% by weight, preferably of from about 30% to about 100% by weight, more preferably of from about 40% to about 100% by weight based on the skin contact layer.

In one embodiment, the skin contact layer comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer, preferably in an amount ratio of 0.1:1 to 1:0.1, more preferably of 0.5:1 to 1:0.5, particularly preferred of 1:1.

In one embodiment, the skin contact layer comprises a blend of at least two polymers based on polysiloxanes which are characterized by different physical properties, preferably in an amount ratio of 0.5:1 to 1:0.5.

In another embodiment, the skin contact layer comprises a blend of a polymer based on polysiloxanes and an acrylate polymer, preferably in an amount ratio of 0.5:1 to 1:0.5.

In one particular embodiment, the skin contact layer comprises a blend of at least two silicone acrylic hybrid polymers which are characterized by different physical properties, preferably in an amount ratio of 0.5:1 to 1:0.5.

In another particular embodiment, the skin contact layer comprises a blend of a silicone acrylic hybrid polymer and a non-hybrid polymer selected from the group consisting of a polymer based on polysiloxanes, a polymer based on polyisobutylenes, a styrene-isoprene-styrene block copolymer, and an acrylate polymer. In this connection, the silicone acrylic hybrid polymer and the non-hybrid polymer may be contained in the solifenacin-containing layer in an amount ratio of from 0.1:1 to 1:0.1, and are preferably contained in an amount ratio of from 0.5:1 to 1:0.5.

In a particular embodiment, the skin contact layer comprises a blend of a silicone acrylic hybrid polymer and a polymer based on polysiloxanes, preferably in an amount ratio of 0.5:1 to 1:0.5.

In another particular embodiment, the skin contact layer comprises a blend of a silicone acrylic hybrid polymer and an acrylate polymer, preferably in an amount ratio of 0.5:1 to 1:0.5.

In another embodiment, the skin contact layer comprises a blend of at least two polyisobutylenes which are characterized by different physical properties, preferably in an amount ratio of 0.5:1 to 1:0.5.

According to certain embodiments, the total amount of polymer contained in the skin contact layer ranges from about 40% to about 100% by weight, preferably from about 50% to about 100% by weight, more preferably from about 60% to about 100% by weight based on the skin contact layer.

The skin contact layer may comprise an active agent. The active agent may be solifenacin, as well. The active agent in the skin contact layer may also be an additional active agent reasonable for an administration together with solifenacin (e.g. rivastigmine).

In a preferred embodiment, the skin contact layer is free of active agent, that is, is prepared without the addition of an active agent.

As mentioned above, the TTS according to the invention may further comprise one or more anti-oxidants. The anti-oxidants may be contained in the solifenacin-containing layer or in an additional skin contact layer or in both the solifenacin-containing layer and the additional skin contact layer.

Active Agent Solifenacin

The TTS according to the invention comprises a therapeutically effective amount of solifenacin. A therapeutically effective amount may vary from about 1 mg to about 150 mg of solifenacin base or an equimolar amount of a pharmaceutically acceptable salt thereof.

In one embodiment of the invention, the solifenacin is contained in an amount of from 2% to 40%, from 3% to 40%, or from 5% to 35%, or of about 5%, about 10%, about 15%, about 20%, about 25%, about 30%, or about 35% by weight based on the solifenacin-containing layer.

In one embodiment of the invention, the solifenacin is contained in the solifenacin-containing layer structure in an amount of from 0.1 $mg/cm^2$ to 5.0 $mg/cm^2$, from 0.1 $mg/cm^2$ to 4.0 $mg/cm^2$, or from 0.2 $mg/cm^2$ to 4.0 mg/cm based on the solifenacin-containing layer.

In certain embodiments, the solifenacin in the solifenacin-containing layer may be included in the form of a pharmaceutically acceptable chemical and morphological form and physical state, such as a pharmaceutically acceptable salt thereof. In one embodiment, the solifenacin-containing layer comprises a pharmaceutically acceptable salt of solifenacin, such as solifenacin hydrochloride. However, it is preferred according to the invention that the solifenacin in the solifenacin-containing layer is included in the form of the free base.

In certain embodiments, the solifenacin has a purity of at least 95%, preferably of at least 98%, and more preferably of at least 99% as determined by quantitative HPLC. Quantitative HPLC may be performed with Reversed-Phase-HPLC with UV detection.

According to certain embodiments, an additional active agent (e.g. rivastigmine) is contained in the solifenacin-containing layer structure, preferably in an amount of from about 0.5 mg/cm² to about 5.0 mg/cm².

Silicone Acrylic Hybrid Polymer

The solifenacin-containing layer structure according to the present invention may comprise a silicone acrylic hybrid polymer. The silicone acrylic hybrid polymer comprises a polymerized hybrid species that includes silicone-based sub-species and acrylate-based sub-species that have been polymerized together. The silicone acrylic hybrid polymer thus comprises a silicone phase and an acrylic phase. Preferably, the silicone acrylic hybrid polymer is a silicone acrylic hybrid pressure-sensitive adhesive.

The silicone acrylic hybrid pressure-sensitive adhesives are usually supplied and used in solvents like n-heptane and ethyl acetate. The solids content of the pressure-sensitive adhesives is usually between 30% and 80%. The skilled person is aware that the solids content may be modified by adding a suitable amount of solvent.

Preferably, the weight ratio of silicone to acrylate in the silicone acrylic hybrid pressure-sensitive adhesive is from 5:95 to 95:5, or from 20:80 to 80:20, more preferably from 40:60 to 60:40, and most preferably the ratio of silicone to acrylate is about 50:50. Suitable silicone acrylic hybrid pressure-sensitive adhesives having a weight ratio of silicone to acrylate of 50:50 are, for example, the commercially available silicone acrylic hybrid pressure-sensitive adhesives 7-6102, Silicone/Acrylate Ratio 50/50, and 7-6302, Silicone/Acrylate Ratio 50/50, supplied in ethyl acetate by Dow Corning.

The preferred silicone acrylic hybrid pressure-sensitive adhesives in accordance with the invention are characterized by a solution viscosity at 25° C. and about 50% solids content in ethyl acetate of more than about 400 cP, or from about 500 cP to about 3,500 cP, in particular from about 1,000 cP to about 3,000 cP, more preferred from about 1,200 cP to about 1,800, or most preferred of about 1,500 cP or alternatively more preferred from about 2,200 cP to about 2,800 cP, or most preferred of about 2,500 cP, preferably as measured using a Brookfield RVT viscometer equipped with a spindle number 5 at 50 RPM.

These silicone acrylic hybrid pressure-sensitive adhesives may also be characterized by a complex viscosity at 0.1 rad/s at 30° C. of less than about 1.0e9 Poise, or from about 1.0e5 Poise to about 9.0e8 Poise, or preferably from about 9.0e5 Poise to about 1.0e7 Poise, or more preferred from about 9.0e5 Poise to about 7.0e6 Poise, or most preferred about 4.0e6 Poise, or alternatively preferably from about 2.0e6 Poise to about 9.0e7 Poise, or more preferred from about 8.0e6 Poise to about 9.0e7 Poise, or most preferred about 1.0e7 Poise, preferably as measured using a Rheometrics ARES rheometer, wherein the rheometer is equipped with 8 mm plates and the gap zeroed.

In one embodiment of the present invention, the transdermal therapeutic system comprises at least two silicone acrylic hybrid polymers selected from at least two of the silicone acrylic hybrid polymer groups:
  silicone acrylic hybrid pressure-sensitive adhesives characterized by a solution viscosity at 25° C. and about 50% solids content in ethyl acetate of from about 1,200 cP to about 1,800 cP, preferably as measured using a Brookfield RVT viscometer equipped with a spindle number 5 at 50 RPM, and
  silicone acrylic hybrid pressure-sensitive adhesives characterized by a solution viscosity at 25° C. and about 50% solids content in ethyl acetate of from about 2,200 cP to about 2,800 cP, preferably as measured using a Brookfield RVT viscometer equipped with a spindle number 5 at 50 RPM.

In another embodiment of the present invention, the transdermal therapeutic system comprises at least two silicone acrylic hybrid polymers selected from at least two of the silicone acrylic hybrid polymer groups:
  silicone acrylic hybrid pressure-sensitive adhesives characterized by a complex viscosity at 0.1 rad/s at 30° C. of from about 9.0e5 Poise to about 7.0e6 Poise, preferably as measured using a Rheometrics ARES rheometer, wherein the rheometer is equipped with 8 mm plates and the gap zeroed, and
  silicone acrylic hybrid pressure-sensitive adhesives characterized by a complex viscosity at 0.1 rad/s at 30° C. of from about 8.0e6 Poise to about 9.0e7 Poise, preferably as measured using a Rheometrics ARES rheometer, wherein the rheometer is equipped with 8 mm plates and the gap zeroed.

To prepare samples for measuring the rheological behavior using a Rheometrics ARES rheometer, between 2 and 3 grams of adhesive solution can be poured onto a SCOTCH-PAK 1022 fluoropolymer release liner and allow to sit for 60 minutes under ambient conditions. To achieve essentially solvent-free films of the adhesive, they can be placed in an oven at 110° C.+/−10° C. for 60 minutes. After removing from the oven and letting equilibrate to room temperature. The films can be removed from the release liner and folded over to form a square. To eliminate air bubbles the films can be compressed using a Carver press. The samples can then be loaded between the plates and are compressed to 1.5+/−0.1 mm at 30° C. The excess adhesive is trimmed and the final gap recorded. A frequency sweep between 0.01 to 100 rad/s can be performed with the following settings: Temperature=30° C.; strain=0.5-1% and data collected at 3 points/decade.

Suitable silicone acrylic hybrid pressure-sensitive adhesives which are commercially available include the PSA series 7-6100 and 7-6300 manufactured and supplied in n-heptane or ethyl acetate by Dow Corning (7-610X and 7-630X; X=1 n-heptane-based/X=2 ethyl acetate-based). For example, the 7-6102 silicone acrylic hybrid PSA having a silicone/acrylate ratio of 50/50 is characterized by a solution viscosity at 25° C. and about 50% solids content in ethyl acetate of 2,500 cP and a complex viscosity at 0.1 rad/s at 30° C. of 1.0e7 Poise. The 7-6302 silicone acrylic hybrid PSA having a silicone/acrylate ratio of 50/50 has a solution viscosity at 25° C. and about 50% solids content in ethyl acetate of 1,500 cP and a complex viscosity at 0.1 rad/s at 30° C. of 4.0e6 Poise.

Depending on the solvent in which the silicone acrylic hybrid pressure-sensitive adhesive is supplied, the arrangement of the silicone phase and the acrylic phase providing a silicone or acrylic continuous external phase and a corresponding discontinuous internal phase is different. If the silicone acrylic hybrid pressure-sensitive adhesive is provided in n-heptane, the composition contains a continuous, silicone external phase and a discontinuous, acrylic internal phase. If the silicone acrylic hybrid pressure-sensitive adhesive is provided in ethyl acetate, the composition contains a continuous, acrylic external phase and a discontinuous, silicone internal phase. After evaporating the solvent in which the silicone acrylic hybrid pressure-sensitive adhesive is provided, the phase arrangement of the resulting pressure-sensitive adhesive film or layer corresponds to the phase arrangement of the solvent-containing adhesive coating composition. For example, in the absence of any substance that may induce an inversion of the phase arrangement in a silicone acrylic hybrid pressure sensitive adhesive composition, a pressure-sensitive adhesive layer prepared from a silicone acrylic hybrid pressure-sensitive adhesive in n-heptane provides a continuous, silicone external phase and a discontinuous, acrylic internal phase, a pressure-sensitive adhesive layer prepared from a silicone acrylic hybrid pressure-sensitive adhesive in ethyl acetate provides a continuous, acrylic external phase and a discontinuous, silicone internal phase. The phase arrangement of the compositions can, for example, be determined in peel force tests with pressure-sensitive adhesive films or layers prepared from the silicone acrylic hybrid PSA compositions which are attached to a siliconized release liner. The pressure-sensitive adhesive film contains a continuous, silicone external phase if the siliconized release liner cannot or can only hardly be removed from the pressure-sensitive adhesive film (laminated to a backing film) due to the blocking of the two silicone surfaces. Blocking results from the adherence of two silicone layers which comprise a similar surface energy. The adhesive shows a good spreading on the siliconized liner and therefore can create a good adhesion to the liner. If the siliconized release liner can easily be removed the pressure-sensitive adhesive film contains a continuous, acrylic external phase. The acrylic adhesive has no good spreading due to the different surface energies and thus has a low or almost no adhesion to the siliconized liner.

According to a preferred embodiment of the invention the silicone acrylic hybrid polymer is a silicone acrylic hybrid pressure-sensitive adhesive obtainable from a silicon-containing pressure-sensitive adhesive composition comprising acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

According to certain embodiments of the invention the silicone acrylic hybrid pressure-sensitive adhesive comprises the reaction product of (a) a silicon-containing pressure-sensitive adhesive composition comprising acrylate or methacrylate functionality, (b) an ethylenically unsaturated monomer, and (c) an initiator. That is, the silicone acrylic hybrid pressure-sensitive adhesive is the product of the chemical reaction between these reactants ((a), (b), and (c)). In particular, the silicone acrylic hybrid pressure-sensitive adhesive includes the reaction product of (a) a silicon-containing pressure-sensitive adhesive composition comprising acrylate or methacrylate functionality, (b) a (meth) acrylate monomer, and (c) an initiator (i.e., in the presence of the initiator). That is, the silicone acrylic hybrid pressure-sensitive adhesive includes the product of the chemical reaction between these reactants ((a), (b), and (c)).

The reaction product of (a) a silicon-containing pressure-sensitive adhesive composition comprising acrylate or methacrylate functionality, (b) an ethylenically unsaturated monomer, and (c) an initiator may contain a continuous, silicone external phase and a discontinuous, acrylic internal phase or the reaction product of (a), (b), and (c) may contain a continuous, acrylic external phase and a discontinuous, silicone internal phase.

The silicon-containing pressure-sensitive adhesive composition comprising acrylate or methacrylate functionality (a) is typically present in the silicone acrylic hybrid pressure-sensitive adhesive in an amount of from 5 to 95, more typically 25 to 75, parts by weight based on 100 parts by weight of the hybrid pressure-sensitive adhesive.

The ethylenically unsaturated monomer (b) is typically present in the silicone acrylic hybrid pressure-sensitive adhesive in an amount of from 5 to 95, more typically 25 to 75, parts by weight based on 100 parts by weight of the hybrid pressure-sensitive adhesive.

The initiator (c) is typically present in the silicone acrylic hybrid pressure-sensitive adhesive in an amount of from 0.005 to 3, more typically from 0.01 to 2, parts by weight based on 100 parts by weight of the hybrid pressure-sensitive adhesive.

According to certain embodiments of the invention the silicon-containing pressure-sensitive adhesive composition comprising acrylate or methacrylate functionality (a) comprises the condensation reaction product of (a1) a silicone resin, (a2) a silicone polymer, and (a3) a silicon-containing capping agent which provides said acrylate or methacrylate functionality. The silicone resin (a1) may also be referred to as silicate resin or silica resin. Preferably, the silicone polymer (a2) is a polysiloxane, preferably polydimethylsiloxane. It is to be understood that (a1) and (a2) form a silicone-based pressure sensitive adhesive by polycondensation, and that the acrylate or methacrylate functionality is introduced by reaction with (a3).

According to certain embodiments of the invention the silicon-containing pressure-sensitive adhesive composition comprising acrylate or methacrylate functionality (a) comprises the condensation reaction product of:
(a1) a silicone resin,
(a2) a silicone polymer, and
(a3) a silicon-containing capping agent which provides said acrylate or methacrylate functionality, wherein said silicon-containing capping agent is of the general formula $XYR'_{b}SiZ_{3-b}$, wherein
X is a monovalent radical of the general formula AE— where E is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer.

According to certain embodiments of the invention the silicon-containing pressure-sensitive adhesive composition comprising acrylate or methacrylate functionality comprises the condensation reaction product of a pressure sensitive adhesive and a silicon-containing capping agent which provides said acrylate or methacrylate functionality. That is, the silicon-containing pressure sensitive adhesive composition comprising acrylate or methacrylate functionality is essentially a pressure sensitive adhesive that has been capped or end blocked with the silicon-containing capping agent which provides said acrylate or methacrylate functionality, wherein the pressure sensitive adhesive comprises the condensation reaction product of the silicone resin and the silicone polymer. Preferably, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst. A wide array of silicone resins and silicone polymers are suitable to make up the pressure sensitive adhesive.

According to certain embodiments of the invention the silicone acrylic hybrid pressure-sensitive adhesive is the reaction product of:
- (a) a silicon-containing pressure-sensitive adhesive composition comprising acrylate or methacrylate functionality that comprises the condensation reaction product of:
  - (a1) a silicone resin,
  - (a2) a silicone polymer, and
  - (a3) a silicon-containing capping agent which provides said acrylate or methacrylate functionality, wherein said silicon-containing capping agent is of the general formula $XYR'_b SiZ_{3-b}$, wherein
    - X is a monovalent radical of the general formula AE- where E is —O— or —NH— and A is an acryl group or a methacryl group,
    - Y is a divalent alkylene radical having from 1 to 6 carbon atoms,
    - R' is a methyl or a phenyl radical,
    - Z is a monovalent hydrolyzable organic radical or a halogen, and
    - b is 0 or 1;
  - wherein the silicone resin and silicone polymer are reacted to form a pressure-sensitive adhesive, wherein the silicon-containing capping agent is introduced prior to, during, or after the silicone resin and silicone polymer are reacted, and wherein:
    - the silicon-containing capping agent reacts with the pressure-sensitive adhesive after the silicone resin and silicone polymer have been condensation reacted to form the pressure-sensitive adhesive; or
    - the silicon-containing capping agent reacts in-situ with the silicone resin and silicone polymer;
- (b) an ethylenically unsaturated monomer; and
- (c) an initiator.

The silicone acrylic hybrid composition used in the present invention may be described by being prepared by a method comprising the steps of:
- (i) providing a silicon-containing pressure-sensitive adhesive composition comprising acrylate or methacrylate functionality that comprises the condensation reaction product of:
  - a silicone resin,
  - a silicone polymer, and
  - a silicon-containing capping agent which provides said acrylate or methacrylate functionality, wherein said silicon-containing capping agent is of the general formula $XYR'_b SiZ_{3-b}$, wherein
    - X is a monovalent radical of the general formula AE- where E is —O— or —NH— and A is an acryl group or a methacryl group,
    - Y is a divalent alkylene radical having from 1 to 6 carbon atoms,
    - R' is a methyl or a phenyl radical,
    - Z is a monovalent hydrolyzable organic radical or a halogen, and
    - b is 0 or 1;
  - wherein the silicone resin and silicone polymer are reacted to form a pressure-sensitive adhesive, wherein the silicon-containing capping agent is introduced prior to, during, or after the silicone resin and silicone polymer are reacted, and wherein:
    - the silicon-containing capping agent reacts with the pressure-sensitive adhesive after the silicone resin and silicone polymer have been condensation reacted to form the pressure-sensitive adhesive; or
    - the silicon-containing capping agent reacts in-situ with the silicone resin and silicone polymer;
- (ii) polymerizing an ethylenically unsaturated monomer and the silicon-containing pressure-sensitive adhesive composition comprising acrylate or methacrylate functionality of step (i) in the presence of an initiator to form a silicone acrylic hybrid composition, optionally at a temperature of from 50° C. to 100° C., or from 65° C. to 90° C.

During the polymerization of the ethylenically unsaturated monomer and the silicon-containing pressure-sensitive adhesive composition comprising acrylate or methacrylate functionality, the silicone to acrylic ratio can be controlled and optimized as desired. The silicone to acrylic ratio can be controlled by a wide variety of mechanisms in and during the method. An illustrative example of one such mechanism is the rate controlled addition of the ethylenically unsaturated monomer or monomers to the silicon-containing pressure-sensitive adhesive composition comprising acrylate or methacrylate functionality. In certain applications, it may be desirable to have the silicone-based sub-species, or the overall silicone content, to exceed the acrylate-based sub-species, or the overall acrylic content. In other applications, it may be desirable for the opposite to be true. Independent of the end application, it is generally preferred, as already described above, that the silicon-containing pressure-sensitive adhesive composition comprising acrylate or methacrylate functionality is preferably present in the silicone acrylic hybrid composition in an amount of from about 5 to about 95, more preferably from about 25 to about 75, and still more preferably from about 40 to about 60 parts by weight based on 100 parts by weight of the silicone acrylic hybrid composition.

According to a certain embodiment of the invention, the silicone acrylic hybrid composition used in the present invention may be described by being prepared by a method comprising the steps of:
- (i) providing a silicon-containing pressure-sensitive adhesive composition comprising acrylate or methacrylate functionality that comprises the condensation reaction product of:
  - a silicone resin,
  - a silicone polymer, and
  - a silicon-containing capping agent which provides said acrylate or methacrylate functionality, wherein said silicon-containing capping agent is of the general formula $XYR'_b SiZ_{3-b}$, wherein
    - X is a monovalent radical of the general formula AE- where E is —O— or —NH— and A is an acryl group or a methacryl group,
    - Y is a divalent alkylene radical having from 1 to 6 carbon atoms,
    - R' is a methyl or a phenyl radical,
    - Z is a monovalent hydrolyzable organic radical or a halogen, and
    - b is 0 or 1;
  - wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.

The silicone acrylic hybrid PSA composition used in the present invention may also be described by being prepared by a method comprising the steps of:
(i) providing a silicon-containing pressure-sensitive adhesive composition comprising acrylate or methacrylate functionality that comprises the condensation reaction product of:
a silicone resin,
a silicone polymer, and
a silicon-containing capping agent which provides said acrylate or methacrylate functionality, wherein said silicon-containing capping agent is of the general formula $XYR'_bSiZ_{3-b}$, wherein
X is a monovalent radical of the general formula AE— where is —O— or —NH— and A is an acryl group or a methacryl group,
Y is a divalent alkylene radical having from 1 to 6 carbon atoms,
R' is a methyl or a phenyl radical,
Z is a monovalent hydrolyzable organic radical or a halogen, and
b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
the silicon-containing capping agent reacts with the pressure-sensitive adhesive after the silicone resin and silicone polymer have been condensation reacted to form the pressure-sensitive adhesive; or
the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) adding a processing solvent, wherein the processing solvent has a higher boiling point than the first solvent, and
(iv) applying heat at a temperature of from 70° C. to 150° C. such that a majority of the first solvent is selectively removed;
(v) removing the processing solvent; and.
(vi) adding a second solvent to form the silicone acrylic hybrid composition, wherein the phase arrangement of the silicone acrylic hybrid composition is selectively controlled by selection of the second solvent.

The silicone resin according to the previous paragraphs may contain a copolymer comprising triorganosiloxy units of the formula $R^X_3SiO_{1/2}$ and tetrafunctional siloxy units of the formula $SiO_{4/2}$ in a ratio of from 0.1 to 0.9, preferably of about 0.6 to 0.9, triorganosiloxy units for each tetrafunctional siloxy unit. Preferably, each $R^X$ independently denotes a monovalent hydrocarbon radical having from 1 to 6 carbon atoms, vinyl, hydroxyl or phenyl groups.

The silicone polymer according to the previous paragraphs may comprise at least one polydiorganosiloxane and is preferably end-capped (end-blocked) with a functional group selected from the group consisting of hydroxyl groups, alkoxy groups, hydride groups, vinyl groups, or mixtures thereof. The diorganosubstituent may be selected from the group consisting of dimethyl, methylvinyl, methylphenyl, diphenyl, methylethyl, (3,3,3-trifluoropropyl) methyl and mixtures thereof. Preferably, the diorganosubstituents contain only methyl groups. The molecular weight of polydiorganosiloxane will typically range from about 50,000 to about 1,000,000, preferably, from about 80,000 to about 300,000. Preferably, the polydiorganosiloxane comprises $AR^XSiO$ units terminated with endblocking $TR^XASiO_{1/2}$ units, wherein the polydiorganosiloxane has a viscosity of from about 100 centipoise to about 30,000,000 centipoise at 25° C., each A radical is independently selected from $R^X$ or halohydrocarbon radicals having from 1 to 6 carbon atoms, each T radical is independently selected from the group consisting of $R^X$, OH, H or $OR^Y$, and each $R^Y$ is independently an alkyl radical having from 1 to 4 carbon atoms.

As an example using forms of the preferred silicone resin and the preferred silicone polymer, one type of pressure sensitive adhesive is made by:
mixing (i) from 30 to 80 inclusive parts by weight of at least one resin copolymer containing silicon-bonded hydroxyl radicals and consisting essentially of $R^X_3SiO_{1/2}$ units and $SiO_{4/2}$ units in a mole ratio of 0.6 to 0.9 $R^X_3SiO_{1/2}$ units for each $SiO_{4/2}$ unit present, (ii) between about 20 and about 70 parts by weight of at least one polydiorganosiloxane comprising $AR^XSiO$ units terminated with endblocking $TR^XASiO_{1/2}$ units, wherein the polydiorganosiloxane has a viscosity of from about 100 centipoise to about 30,000,000 centipoise at 25° C. and each $R^X$ is a monovalent organic radical selected from the group consisting of hydrocarbon radicals of from 1 to 6 inclusive carbon atoms, each A radical is independently selected from $R^X$ or halohydrocarbon radicals having from 1 to 6 inclusive carbon atoms, each T radical is independently selected from the group consisting of $R^X$, OH, H or $OR^Y$, and each $R^Y$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (i), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention.

The silicon-containing capping agent according to the previous paragraphs may be selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof and may be described as to be of the general formula $XYR'_bSiZ_{3-b}$, wherein X is a monovalent radical of the general formula AE- where E is —O— or —NH— and A is n acryl group or a methacryl group, Y is a divalent alkylene radical having from 1 to 6 carbon atoms, R' is a methyl or a phenyl radical, Z is a monovalent hydrolyzable organic radical or a halogen, and b is 0, 1 or 2. Preferably, the monovalent hydrolyzable organic radical is of the general formula R"0—where R" is an alkylene radical. Most preferably, this particular endblocking agent is selected from the group of 3-methaeryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-methacryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl)trimethoxysilane, (methacryloxymethyl)dimethylethoxysilane, (methacryloxymethyl)methyldiethoxysilane, methacryloxymethyltriethoxysilane, methacryloxy-propyltriisopropoxysilane, 3-methacryloxypropyldimethylsilazane, 3-acryloxy-propyldimethylchlorosilane, 3-acryloxypropyldichlorosilane, 3-acryloxypropyl-trichlorosilane, 3-acryloxypropyldimethylmethoxysilane, 3-acryloxy-propylmethyldimethoxysilane, 3-acryloxypropyltrimethoxysilane, 3-acryloxypropyl-dimethylsilazane, and combinations thereof.

The ethylenically unsaturated monomer according to the previous paragraphs can be any monomer having at least one carbon-carbon double bond. Preferably, the ethylenically unsaturated monomer according to the previous paragraphs may be a compound selected from the group consisting of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms. The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl meth-acrylate, tert-butyl methacrylate, hexyl methacrylate, 2-ethyl-hexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

It is to be understood that the ethylenically unsaturated monomer used for preparing the silicone acrylic hybrid pressure sensitive adhesive may be more than one ethylenically unsaturated monomer. That is, a combination of ethylenically unsaturated monomers may be polymerized, more specifically co-polymerized, along with the silicon-containing pressure sensitive adhesive composition comprising acrylate or methacrylate functionality and the initiator. According to a certain embodiment of the invention, the silicone acrylic hybrid pressure-sensitive adhesive is prepared by using at least two different ethylenically unsaturated monomers, preferably selected from the group of 2-ethylhexyl acrylate and methyl acrylate, preferably in a ratio of from 40:60 to 70:30, more preferably in a ratio of from 65:35 to 55:45 or of from 55:45 to 45:50, particular preferred in a ratio of 50% 2-ethylhexyl acrylate and 50% methyl acrylate, or in a ratio of 60% 2-ethylhexyl acrylate and 40% methyl acrylate, as the acrylic monomer.

The initiator according to the previous paragraphs may be any substance that is suitable to initiate the polymerization of the silicon-containing pressure sensitive adhesive composition comprising acrylate or methacrylate functionality and the ethylenically unsaturated monomer to form the silicone acrylic hybrid. For example, free radical initiators selected from the group of peroxides, azo compounds, redox initiators, and photo-initiators may be used.

Further suitable silicone resins, silicone polymers, silicon-containing capping agents, ethylenically unsaturated monomers, and initiators that can be used in accordance with the previous paragraphs are detailed in WO 2007/145996, EP2 599 847 A1, and WO 2016/130408.

According to a certain embodiment of the invention, the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.

According to a certain other embodiment of the invention, the silicone acrylic hybrid polymer comprises a reaction product of a silicone polymer, a silicone resin and an acrylic polymer, wherein the silicone resin contains triorganosiloxy units $R_3SiO_{1/2}$ where R is an organic group, and tetrafunctional siloxy units $SiO_{4/2}$ in a mole ratio of from 0.1 to 0.9 $R_3SiO_{1/2}$ units for each $SiO_{4/2}$.

The acrylic polymer may comprise at least an alkoxysilyl functional monomer, polysiloxane-containing monomer, halosilyl functional monomer or alkoxy halosilyl functional monomer. Preferably, the acrylic polymer is prepared from alkoxysilyl functional monomers selected from the group consisting of trialkoxylsilyl (meth)acrylates, dialkoxyalkylsilyl (meth)acrylates, and mixtures thereof, or comprises end-capped alkoxysilyl functional groups. The alkoxysilyl functional groups may preferably be selected from the group consisting of trimethoxylsilyl groups, dimethoxymethylsilyl groups, triethoxylsilyl, diethoxymethylsilyl groups and mixtures thereof.

The acrylic polymer may also be prepared from a mixture comprising polysiloxane-containing monomers, preferably from a mixture comprising polydimethylsiloxane mono(meth)acrylate.

The silyl functional monomers will typically be used in amounts of from 0.2 to 20% by weight of the acrylic polymer, more preferably the amount of silyl functional monomers will range from about 1.5 to about 5% by weight of the acrylic polymer.

The amount of polysiloxane-containing monomer will typically be used in amounts of from 1.5 to 50% by weight of the acrylic polymer, more preferably the amount of polysiloxane-containing monomers will range from 5 to 15% by weight of the acrylic polymer.

Alternatively, the acrylic polymer comprises a block or grafted copolymer of acrylic and polysiloxane. An example of a polysiloxane block copolymer is polydimethylsiloxane-acrylic block copolymer. The preferred amount of siloxane block is 10 to 50% by weight of the whole block polymer.

The acrylic polymer comprises alkyl (meth)acrylate monomers. Preferred alkyl (meth)acrylates which may be used have up to about 18 carbon atoms in the alkyl group, preferably from 1 to about 12 carbon atoms in the alkyl group. Preferred low glass transition temperature (Tg) alkyl acrylate with a homopolymer Tg of less than about 0° C. have from about 4 to about 10 carbon atoms in the alkyl group and include butyl acrylate, amyl acrylate, hexyl acrylate, 2-ethylhexyl acrylate, octyl acrylate, isooctyl acrylate, decyl acrylate, isomers thereof, and combinations thereof. Particularly preferred are butyl acrylate, 2-ethylhexyl acrylate and isooctyl acrylate. The acrylic polymer components may further comprise (meth)acrylate monomers having a high Tg such as methyl acrylate, ethyl acrylate, methyl methacrylate and isobutyl methacrylate.

The acrylic polymer component may further comprise a polyisobutylene group to improve cold flow properties of the resultant adhesive.

The acrylic polymer components may comprise nitrogen-containing polar monomers. Examples include N-vinyl pyrrolidone, N-vinyl caprolactam, N-tertiary octyl acrylamide, dimethyl acrylamide, diacetone acrylamide, N-tertiary butyl acrylamide, N-isopropyl acrylamide, cyanoethylacrylate, N-vinyl acetamide and N-vinyl formamide.

The acrylic polymer component may comprise one or more hydroxyl containing monomers such as 2-hydroxyethyl acrylate, 2-hydroxyethyl methacrylate, hydroxypropyl acrylate and/or hydroxypropyl methacrylate.

The acrylic polymer components may, if desired, comprise carboxylic acid containing monomers. Useful carboxylic acids preferably contain from about 3 to about 6 carbon atoms and include, among others, acrylic acid, methacrylic acid, itaconic acid, β-carboxyethyl acrylate and the like. Acrylic acid is particularly preferred.

Other useful, well known co-monomers include vinyl acetate, styrene, cyclohexyl acrylate, alkyl di(meth)acrylates, glycidyl methacrylate and allyl glycidyl ether, as well as macromers such as, for example, poly(styryl)methacrylate.

One acrylic polymer component that can be used in the practice of the invention is an acrylic polymer that comprises from about 90 to about 99.5% by weight of butyl acrylate and from about 0.5 to about 10% by weight dimethoxymethylsilyl methacrylate.

According to a certain embodiment of the invention the silicone acrylic hybrid polymer may be prepared by a) reacting silicone polymer with silicone resin to form a resultant product, b) reacting the resultant product of a) with an acrylic polymer containing reactive functionality, wherein the components are reacted in an organic solvent.

According to a certain embodiment of the invention the silicone acrylic hybrid polymer may be prepared by a) reacting a silicone resin with an acrylic polymer containing reactive functionality to form a resultant product, b) reacting the resultant product of a) with silicone polymer, wherein the components are reacted in an organic solvent.

According to a certain embodiment of the invention the silicone acrylic hybrid polymer may be prepared by a) reacting a silicone polymer with an acrylic polymer containing reactive functionality to form a resultant product, b) reacting the resultant product of a) with silicone resin, wherein the components are reacted in an organic solvent.

Further suitable acrylic polymers, silicone resins, and silicone polymers that can be used for chemically reacting together a silicone polymer, a silicone resin and an acrylic polymer to provide a silicone acrylic hybrid polymer in accordance with the previous paragraphs are detailed in WO2010/124187.

According to certain embodiments of the invention, the silicone acrylic hybrid polymer used in the TTS is blended with one or more non-hybrid polymers, preferably the silicone acrylic hybrid polymer is blended with one or more non-hybrid pressure sensitive adhesives (e.g. pressure-sensitive adhesives based on polysiloxanes or acrylates).

Non-Hybrid Polymers

According to a certain embodiment of the invention, the TTS comprises at least one non-hybrid polymer (e.g. a polymer based on polysiloxanes). Non-hybrid polymers (e.g. non-hybrid pressure-sensitive adhesives) are polymers (e.g. polymer-based pressure-sensitive adhesives) which do not include a hybrid species. Preferred are non-hybrid polymers (e.g. non-hybrid pressure-sensitive adhesives) based on polysiloxanes, acrylates, polyisobutylenes, or styrene-isoprene-styrene block copolymers.

The non-hybrid polymers (e.g. the non-hybrid pressure-sensitive adhesives) may be contained in the active agent-containing layer structure and/or in the adhesive overlay.

Non-hybrid pressure-sensitive adhesives are usually supplied and used in solvents like n-heptane and ethyl acetate. The solids content of the pressure-sensitive adhesives is usually between 30% and 80%.

Suitable non-hybrid polymers according to the invention are commercially available e.g. under the brand names BIO-PSAs (pressure-sensitive adhesives based on polysiloxanes), Oppanol™ (polyisobutylenes), JSR-SIS (a styrene-isoprene-styrene copolymer) or Duro-Tak™ (acrylic polymers).

Polymers based on polysiloxanes may also be referred to as silicone-based polymers or polysiloxane-based polymers. These polymers based on polysiloxanes are preferably pressure sensitive adhesives based on polysiloxanes. Pressure-sensitive adhesives based on polysiloxanes may also be referred to as silicone-based adhesives, silicone-based pressure-sensitive adhesives, polysiloxane-based adhesives, or polysiloxane-based pressure-sensitive adhesives. These pressure-sensitive adhesives based on polysiloxanes provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin (also referred to as silicate resin), a pressure-sensitive adhesive based on polysiloxane is prepared wherein for amine stability the residual silanol functionality is additionally capped with trimethylsiloxy groups. The silanol end blocked polydimethylsiloxane content contributes to the viscous component of the viscoelastic behavior, and impacts the wetting and the spreadability properties of the adhesive. The resin acts as a tackifying and reinforcing agent, and participates in the elastic component. The correct balance between silanol end blocked polydimethylsiloxane and resin provides for the correct adhesive properties.

In view of the above, silicone-based polymers, and in particular silicone-based pressure sensitive adhesives, are generally obtainable by polycondensation of silanol end-blocked polydimethylsiloxane with a silicate resin. Amine-compatible silicone-based polymers, and in particular amine-compatible silicone-based pressure sensitive adhesives, can be obtained by reacting the silicone-based polymer, in particular the silicone-based pressure sensitive adhesive, with trimethylsilyl (e.g. hexamethyldisilazane) in order to reduce the silanol content of the polymer. As a result, the residual silanol functionality is at least partly, preferably mostly or fully capped with trimethylsiloxy groups.

As indicated above, the tackiness of the silicone-based polymer may be modified by the resin-to-polymer ratio, i.e. the ratio of the silanol endblocked polydimethylsiloxane to the silicate resin, which is preferably in the range of from 70:30 to 50:50, preferably from 65:35 to 55:45. The tackiness will be increased with increasing amounts of the polydimethylsiloxane relative to the resin. High tack silicone-based polymers preferably have a resin-to-polymer ratio of 55:45, medium tack silicone-based polymers preferably have a resin-to-polymer ratio of 60:40, and low tack silicone-based polymers preferably have a resin-to-polymer ratio of 65:35. High tack silicone-based polymers preferably have a complex viscosity at 0.01 rad/s and 30° C. of about $5\times10^6$ Poise, medium tack silicone-based polymers preferably have a complex viscosity at 0.01 rad/s and 30° C. of about $5\times10^7$ Poise, and low tack silicone-based polymers preferably have a complex viscosity at 0.01 rad/s and 30° C. of about $5\times10^8$ Poise. High tack amine-compatible silicone-based polymers preferably have a complex viscosity at 0.01 rad/s and 30° C. of about $5\times10^6$ Poise, medium tack amine-compatible silicone-based polymers preferably have a complex viscosity at 0.01 rad/s and 30° C. of about $5\times10^8$ Poise, and low tack amine-compatible silicone-based polymers preferably have a complex viscosity at 0.01 rad/s and 30° C. of about $5\times10^9$ Poise.

Examples of silicone-based PSA compositions which are commercially available include the standard BIO-PSA series (7-4400, 7-4500 and 7-4600 series) and the amine compatible (endcapped) BIO-PSA series (7-4100, 7-4200 and 7-4300 series) manufactured and typically supplied in n-heptane or ethyl acetate by Dow Corning. For example, BIO-PSA 7-4201 is characterized by a solution viscosity at 25° C. and about 60% solids content in heptane of 450 mPa s and a complex viscosity at 0.01 rad/s at 30° C. of $1\times10^8$ Poise. BIO-PSA 7-4301 has a solution viscosity at 25° C. and about 60% solids content in heptane of 500 mPa s and a complex viscosity at 0.01 rad/s at 30° C. of $5\times10^6$ Poise.

The pressure-sensitive adhesives based on polysiloxanes are supplied and used in solvents like n-heptane, ethyl acetate or other volatile silicone fluids. The solids content of pressure-sensitive adhesives based on polysiloxanes in solvents is usually between 60 and 85%, preferably between 70 and 80% or between 60 and 75%. The skilled person is aware that the solids content may be modified by adding a suitable amount of solvent.

Pressure-sensitive adhesives based on polysiloxanes, which are, e.g., available from Dow Corning, may e obtained according to the following scheme:

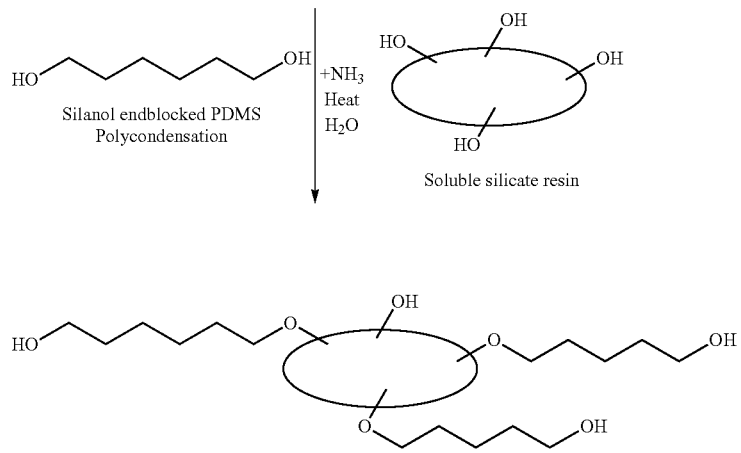

Such pressure-sensitive adhesives based on polysiloxanes are available from Dow Corning, e.g., under the tradenames BIO-PSA 7-4401, BIO-PSA-7-4501, or BIO-PSA 7-4601, which are provided in the solvent n-heptane (indicated by the code "01"), or under the tradenames BI-PSA 7-4402, BIO-PSA 7-4502, and BI 7-4602, which are provided in the solvent ethyl acetate (indicated by the code "02"). Typical solids contents in the solvent are in the range of from 60 to 75%. The code "44" indicates a resin-to-polymer ratio of 65:35 resulting in a low tackiness, the code "45" indicates a resin-to-polymer ratio of 60:40 resulting in medium tackiness, the code "46" indicates a resin-to-polymer ratio of 55:45 resulting in high tackiness.

Amine-compatible pressure-sensitive adhesives based on polysiloxanes, which are, e.g., available from Dow Corning may be obtained according to the following scheme:

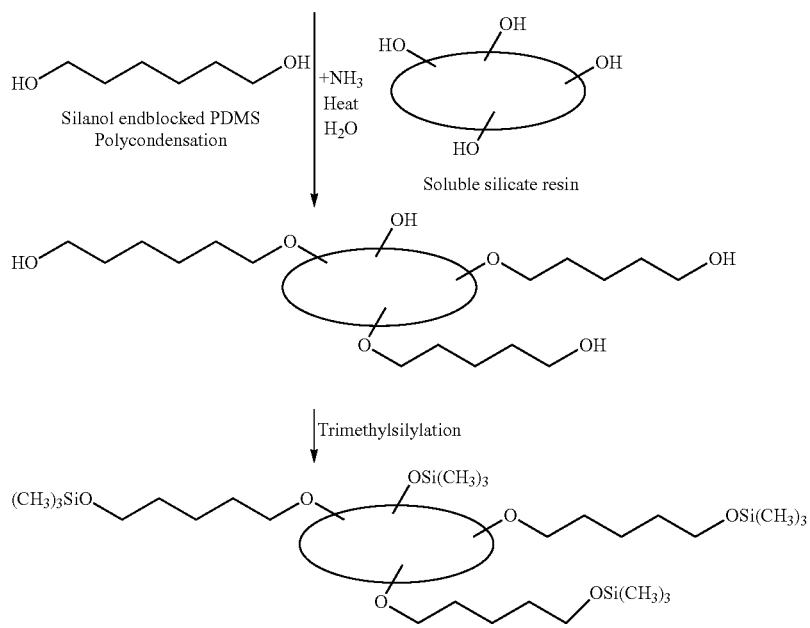

Such amine-compatible pressure-sensitive adhesives based on polysiloxanes are available from Dow Corning, e.g., under the tradenames BIO-PSA 7-4101, BIO-PSA-7-4201, or BIO-PSA 7-4301, which are provided in the solvent n-heptane (indicated by the code "01"), or under the tradenames BIO-PSA 7-4102, BIO-PSA 7-4202, and BIO 7-4302, which are provided in the solvent ethyl acetate (indicated by the code "02"). Typical solids contents in the solvent are in the range of from 60 to 75%. The code "41" indicates a resin-to-polymer ratio of 65:35 resulting in a low tackiness, the code "42" indicates a resin-to-polymer ratio of 60:40 resulting in medium tackiness, the code "43" indicates a resin-to-polymer ratio of 55:45 resulting in high tackiness.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s, or of about 450 mPa s or of about 500 mPa s, preferably as measured using a Brookfield RVT viscometer equipped with a spindle number 5 at 50 rpm. Theses may also be characterized by a complex viscosity at 0.01 rad/s at 30° C. of less than about $1 \times 10^9$ Poise or from about $1 \times 10^5$ to about $9 \times 10^8$ Poise, or of about $1 \times 10^8$ Poise, or of about $5 \times 10^6$ Poise, preferably as measured using a Rheometrics ARES rheometer, wherein the rheometer is equipped with 8 mm plates and the gap zeroed.

In one embodiment of the invention, the solifenacin-containing layer structure comprises at least one pressure-sensitive adhesive based on polysiloxanes characterized by a solution viscosity at 25° C. and about 60% solids content in n-heptane of from about 200 mPa s to about 700 mPa s, preferably as measured using a Brookfield RVT viscometer equipped with a spindle number 5 at 50 RPM, and at least one silicone acrylic hybrid pressure-sensitive adhesive is characterized by a solution viscosity at 25° C. and about 50% solids content in ethyl acetate of from about 1,200 mPa s to about 1,800 mPa s, preferably as measured using a Brookfield RVT viscometer equipped with a spindle number 5 at 50 RPM.

In another embodiment of the invention, the solifenacin-containing layer structure comprises at least one pressure-sensitive adhesive based on polysiloxanes characterized by a solution viscosity at 25° C. and about 60% solids content in n-heptane of from about 200 mPa s to about 700 mPa s, preferably as measured using a Brookfield RVT viscometer equipped with a spindle number 5 at 50 RPM, and at least one silicone acrylic hybrid pressure-sensitive adhesive is characterized by a solution viscosity at 25° C. and about 50% solids content in ethyl acetate of from about 2,200 mPa s to about 2,800 mPa s, preferably as measured using a Brookfield RVT viscometer equipped with a spindle number 5 at 50 RPM.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. A preferred example for a polyisobutylene combination is B10/B10 in a ratio of 85/15. Oppanol® B100 has a viscosity average molecular weight $M_v$ of 1,110,000, and a weight average molecular weight $M_w$ of 1,550,000, and an average molecular weight distribution $M_w/M_n$ of 2.9. Oppanol® B10 has a viscosity average molecular weight $M_v$ of 40,000, and a weight average molecular weight $M_w$ of 53,000, and an average molecular weight distribution $M_w/M_n$ of 3.2. In certain embodiments, polybutene may be added to the polyisobutylenes. The solids content of polyisobutylenes in solvents is usually between 30 and 50%, preferably between 35 and 40%. The skilled person is aware that the solids content may be modified by adding a suitable amount of solvent.

Pressure-sensitive adhesives based on acrylates may also be referred to as acrylate-based pressure-sensitive adhesives, or acrylate pressure-sensitive adhesives. Pressure-sensitive adhesives based on acrylates may have a solids content preferably between 30% and 60%. Such acrylate-based pressure-sensitive adhesives may or may not comprise functional groups such as hydroxy groups, carboxylic acid groups, neutralized carboxylic acid groups and mixtures thereof. Thus, the term "functional groups" in particular refers to hydroxy- and carboxylic acid groups, and deprotonated carboxylic acid groups.

Corresponding commercial products are available e.g. from Henkel under the tradename Duro Tak®. Such acrylate-based pressure-sensitive adhesives are based on monomers selected from one or more of acrylic acid, butylacrylate, 2-ethylhexylacrylate, glycidylmethacrylate, 2-hydroxyethylacrylate, methylacrylate, methylmethacrylate, t-octylacrylamide and vinylacetate, and are provided in ethyl acetate, heptanes, n-heptane, hexane, methanol, ethanol, isopropanol, 2,4-pentanedione, toluene or xylene or mixtures thereof. Suitable acrylate-based pressure-sensitive adhesives are based on monomers selected from two or more of acrylic acid, butylacrylate, 2-ethylhexylacrylate, glycidylmethacrylate, 2-hydroxyethylacrylate, methylacrylate, methylmethacrylate, t-octylacrylamide and vinylacetate.

In one embodiment, the at least one polymer is an acrylate-based pressure-sensitive adhesive, which is a copolymer based on 2-ethylhexylacrylate, 2-hydroxyethylacrylate and vinylacetate.

Specific acrylate-based pressure-sensitive adhesives are available as:
  Duro-Tak™ 87-4287 (a copolymer based on vinyl acetate, 2-ethylhexyl-acrylate, and 2-hydroxyethyl-acrylate provided as a solution in ethyl acetate without cross-linking agent),
  Duro-Tak™ 387-2287 or Duro-Tak™ 87-2287 (a copolymer based on vinyl acetate, 2-ethylhexyl-acrylate, 2-hydroxyethyl-acrylate and glycidyl-methacrylate provided as a solution in ethyl acetate without cross-linking agent),
  Duro-Tak™ 387-2516 or Duro-Tak™ 87-2516 (a copolymer based on vinyl acetate, 2-ethylhexyl-acrylate, 2-hydroxyethyl-acrylate and glycidyl-methacrylate provided as a solution in ethyl acetate, ethanol, n-heptane and methanol with a titanium cross-linking agent),
  Duro-Tak™ 387-2051 or Duro-Tak™ 87-2051 (a copolymer based on acrylic acid, butylacrylate, 2-ethylhexylacrylate and vinyl acetate, provided as a solution in ethyl acetate and heptane),
  Duro-Tak™ 387-2353 or Duro-Tak™ 87-2353 (a copolymer based on acrylic acid, 2-ethylhexylacrylate, glycidylmethacrylate and methylacrylate, provided as a solution in ethyl acetate and hexane),
  Duro-Tak™ 87-4098 (a copolymer based on 2-ethylhexyl-acrylate and vinyl acetate, provided as a solution in ethyl acetate).

Additional polymers may also be added to enhance cohesion and/or adhesion.

Certain polymers in particular reduce the cold flow and are thus in particular suitable as auxiliary polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prevented by the addition of certain polymers. A basic acrylate polymer (e.g. Eudragit® E100) may e.g. be used to reduce the cold flow. Thus, in certain embodiments, the matrix layer composition comprises additionally a basic polymer, in particular an amine-functional acrylate as e.g. Eudragit® E100. Eudragit® E100 is a cationic copolymer based on dimethylaminoethyl methacrylate, butyl methacrylate, and methyl methacrylate with a ratio of 2:1:1. The monomers are randomly distributed along the copolymer chain. Based on SEC method, the weight average molar mass (Mw) of Eudragit® E100 is approximately 47,000 g/mol. Further, auxiliary polymers such as Plastoid B, Eudragits, Chitosan, celluloses and derivatives thereof, and polystyrene may be useful to increase the dryness of the adhesive (e.g. the matrix layer).

Release Characteristics

The TTS in accordance with the invention are designed for transdermally administering solifenacin to the systemic circulation for a predefined extended period of time (e.g. at least or about 24 hours), preferably for at least or about 72 hours.

In one aspect, the TTS according to the invention as described above provide a mean release rate of solifenacin of 2 to 12 mg/day, preferably of 3 to 10 mg/day, and more preferably of 3.5 to 6.75 mg/day, preferably over at least 24 hours, at least 48 hours, at least 72 hours, or about 84 hours of administration.

In certain embodiments, the TTS according to the invention as described above provide a cumulative permeated amount of solifenacin as measured in a Franz diffusion cell with dermatomed human skin of about 0.1 µg/cm$^2$ to about 2.0 mg/cm$^2$, preferably of about 0.2 mg/cm$^2$ to about 1.5 mg/cm$^2$, more preferably of 0.3 mg/cm$^2$ to 1.2 mg/cm$^2$ over a time period of 72 hours.

According to certain embodiments, the TTS according to the invention as described above provide a cumulative skin permeation rate of solifenacin over 72 hours as measured in a Franz diffusion cell with dermatomed human skin of about 1 µg/cm$^2$-hr to about 30 µg/cm$^2$-hr, preferably of about 2 µg/cm$^2$-hr to about 20 µg/cm$^2$-hr, more preferably of about 3 µg/cm$^2$-hr to about 20 µg/cm$^2$-hr.

In certain embodiments, the TTS according to the invention as described above release more than 25% by weight of the amount of solifenacin contained in the transdermal therapeutic system over a period of administration of 72 hours, preferably determined by measuring the permeated amount of solifenacin in a Franz diffusion cell with dermatomed human skin with a thickness of 500 µm, when a phosphate buffer solution pH 5.5 with 0.1% saline azide as antibacteriological agent is used at a temperature of 32±1° C. In certain preferred embodiments, the TTS according to the invention release more than 30%, preferably more than 50%, more preferably more than 70% by weight of the amount of solifenacin contained in the transdermal therapeutic system over a period of administration of 72 hours.

Method of Treatment/Medical Use

In accordance with a specific aspect of the present invention, the TTS according to the invention is for use in a method of treatment, preferably for use in a method of treating overactive bladder with symptoms of urge urinary incontinence, urgency, and urinary frequency pain.

According to certain aspects of the present invention, the TTS is for use in a method of treatment, wherein the transdermal therapeutic system is applied on the skin of a patient for at least of about 24 hours, for more than 24 hours, for at least or about 48 hours, for at least or about 72 hours, or for about 84 hours.

According to one aspect, the invention relates to the use of a TTS according to the present invention for the manufacture of a medicament. In particular, the invention relates to the use of a TTS according to the present invention for the manufacture of a medicament for treating overactive bladder with symptoms of urge urinary incontinence, urgency, and urinary frequency pain, which preferably is applied to the skin of a patient for at least of about 24 hours, for more than 24 hours, for at least or about 48 hours, for at least or about 72 hours, or for about 84 hours.

According to another aspect, the present invention relates to a method of treatment. Preferably, the present invention relates to a method of treating overactive bladder with symptoms of urge urinary incontinence, urgency, and urinary frequency pain by applying to the skin of a patient a transdermal therapeutic system according to the invention. In this connection, the TTS as described above is preferably applied to the skin of a patient for at least of about 24 hours, for more than 24 hours, for at least or about 48 hours, for at least or about 72 hours, or for about 84 hours.

According to another aspect, the present invention relates to a method of reducing the peripheral side effects induced by rivastigmine by applying to the skin of a patient a TTS as described above, preferably for at least of about 24 hours, for more than 24 hours, for at least or about 48 hours, for at least or about 72 hours, or for about 84 hours.

According to a certain aspect of the invention, wherein the TTS comprises a therapeutically effective amount of rivastigmine in addition to the solifenacin, the TTS according to the invention is for use in a method of preventing, treating, or delaying of progression of Alzheimer's disease, dementia associated with Parkinson's disease, and/or symptoms of traumatic brain injury, or for use in a method of treating mild to moderate dementia caused by Alzheimer's or Parkinson's disease.

Thus, according to a certain aspect, the invention relates to use of a TTS according to the present invention, wherein the TTS comprises a therapeutically effective amount of rivastigmine in addition to the solifenacin, for the manufacture of a medicament for preventing, treating, or delaying of progression of Alzheimer's disease, dementia associated with Parkinson's disease, and/or symptoms of traumatic brain injury, or for treating mild to moderate dementia caused by Alzheimer's or Parkinson's disease, which preferably is applied to the skin of a patient for at least of about 24 hours, for more than 24 hours, for at least or about 48 hours, for at least or about 72 hours, or for about 84 hours.

Thus, according to a certain aspect, the invention relates to a method of preventing, treating, or delaying of progression of Alzheimer's disease, dementia associated with Parkinson's disease, and/or symptoms of traumatic brain injury, or a method of treating mild to moderate dementia caused by Alzheimer's or Parkinson's disease by applying to the skin of a patient a TTS as described above, wherein the TTS comprises a therapeutically effective amount of rivastigmine in addition to the solifenacin. In this connection, the TTS is preferably applied to the skin of a patient for at least of about 24 hours, for more than 24 hours, for at least or about 48 hours, for at least or about 72 hours, or for about 84 hours.

Method of Manufacture

The invention further relates to a method of manufacture of a transdermal therapeutic system according to the invention comprising the steps of:

1) providing a solifenacin-containing coating composition comprising
   a) solifenacin (e.g. solifenacin base) and optionally an additional active agent (e.g. rivastigmine base),
   b) optionally a solvent (e.g. ethanol), 2) coating the solifenacin-containing coating composition onto a release liner in an amount to provide the desired area weight, 3) drying the coated solifenacin-containing coating composition to provide the solifenacin-containing layer, 4) laminating the solifenacin-containing layer to a backing layer to provide a solifenacin-containing layer structure, 5) optionally providing an additional skin contact layer by coating and drying an active agent-free coating composition or an active agent-containing coating composition according to steps 2 and 3, removing the release liner of the solifenacin-containing layer and laminating the adhesive side of the skin contact layer onto the adhesive side of the solifenacin-containing layer to provide a solifenacin-containing layer structure, 6) punching the individual systems from the solifenacin-containing layer structure, 7) optionally adhering to the individual systems an active-free self-adhesive layer structure comprising also a backing layer and an active agent-free pressure-sensitive adhesive layer and which is larger than the individual systems of solifenacin-containing self-adhesive layer structure, wherein at least one polymer is added to the solifenacin-containing coating composition in step 1, or, if an additional skin contact layer is provided, to the coating composition in step 5, or to both the solifenacin-containing coating composition in step 1 and to the coating composition in step 5.

In a preferred embodiment, the at least one polymer is a pressure-sensitive adhesive polymer and is provided as a solution, preferably in ethyl acetate, n-heptane or hexane.

In one embodiment, in step 1) solifenacin is present in the form of solifenacin base and is combined with the at least one polymer in ethyl acetate, n-heptane, or hexane to provide the solifenacin-containing coating composition.

In one embodiment, in step 1) solifenacin is present in the form of solifenacin base and is dissolved in ethanol and subsequently combined with the at least one polymer in n-heptane or ethyl acetate to provide the solifenacin-containing coating composition.

In one embodiment, in step 5), the additional skin contact layer is provided by coating and drying an active agent-free coating composition comprising a pressure-sensitive adhesive polymer (e.g. a pressure-sensitive adhesive based on polysiloxane or a silicone acrylic hybrid pressure-sensitive adhesive), preferably in ethyl acetate, n-heptane or hexane.

In step 3) and optionally in step 5) of the above method of manufacture, drying is performed preferably at a temperature of from 20 to 90° C.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Examples 1A, 1B

Coating Composition

The formulations of the solifenacin base-containing coating compositions are summarized below.

TABLE 1

| Ingredient (Trade Name) | Ex. 1a Amt [g] | Ex. 1a Solids [%] | Ex. 1b Amt [g] | Ex. 1b Solids [%] |
|---|---|---|---|---|
| Solifenacin base | 0.8 | 5 | 0.8 | 5 |
| Silicone acrylic hybrid PSA in n-heptane Solids content of 50% by weight (SilAc-PSA 7-6301 from Dow Corning Healthcare) | 29.3 | 95 | — | — |
| Silicone acrylic hybrid PSA in ethyl acetate Solids content of 50% by weight (SilAc-PSA 7-6302 from Dow Corning Healthcare) | — | — | 29.3 | 95 |
| Total | 30.0 | 100.0 | 30.0 | 100.0 |
| Area Weight [g/m$^2$] | | 93.6 | | 93.2 |
| Loading API [µg/cm$^2$] | | 468 | | 466 |

Preparation of the Coating Composition

The silicone acrylic hybrid pressure-sensitive adhesive in the form of a mixture in n-heptane (Ex. 1a) or in ethyl acetate (Ex. 1b) having a solids content of 50% by weight was added to a suitable mixing vessel. solifenacin base was subsequently added to the mixing vessel under stirring and the mixture was stirred for approx. 2 hours to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m$^2$. The dried film was then laminated with a backing layer (polyethylenterephthalate (PET) foil 19 µm) to provide the solifenacin-containing self-adhesive layer structure.

Preparation of the TTS (all Examples)

The individual systems (TTS) were then punched out from the solifenacin-containing self-adhesive layer structure. In specific embodiments a TTS as described above can be provided with an adhesive overlay, i.e. a further self-adhesive layer structure of larger surface area, preferably with rounded corners, comprising a pressure-sensitive adhesive matrix layer which is free of active ingredient and a preferably skin-colored backing layer. The TTSs are then punched out and sealed into pouches of the primary packaging material.

Examples 2A, 2B

Coating Composition

The formulations of the solifenacin base-containing coating compositions are summarized below.

TABLE 2

| Ingredient (Trade Name) | Ex. 2a Amt [g] | Ex. 2a Solids [%] | Ex. 2b Amt [g] | Ex. 2b Solids [%] |
|---|---|---|---|---|
| Solifenacin base | 1.6 | 10 | 1.87 | 10 |
| Polysiloxane-based PSA in ethylacetate Solids content of 60% by weight (BIO-PSA 7-4302 from Dow Corning Healthcare) | 12.0 | 45 | — | — |
| Polysiloxane-based PSA in n-heptane Solids content of 73% by weight (BIO-PSA 7-4301 from Dow Corning Healthcare) | — | — | 10.33 | 40 |
| Polysiloxane-based PSA in ethylacetate Solids content of 60% by weight (BIO-PSA 7-4202 from Dow Corning Healthcare) | 12.0 | 45 | — | — |
| Polysiloxane-based PSA in n-heptane Solids content of 73% by weight (BIO-PSA 7-4201 from Dow Corning Healthcare) | — | — | 12.8 | 50 |
| Total | 25.6 | 100.0 | 25.0 | 100.0 |
| Area Weight [g/m$^2$] | | 102.3 | | 96.1 |
| Loading API [µg/cm$^2$] | | 1023 | | 961 |

Preparation of the Coating Composition

Solifenacin base, the high tack silicone-based adhesive in the form of a mixture in ethylacetate having a solids content of 60% by weight (Ex. 2a), or in n-heptane having a solids content of 73% by weight (Ex. 2b), and the medium tack silicone-based adhesive in the form of a mixture in ethylacetate having a solids content of 60% by weight (Ex. 2a), or in n-heptane having a solids content of 73% by weight (Ex. 2b), were added to a suitable mixing vessel. The mixture was stirred for approx. 2 hours to provide the solifenacin-containing coating composition. For Example 2b, the mixture of solifenacin base and the high tack silicone-based adhesive in the form of a mixture in n-heptane having a solids content of 73% by weight was homogenized for approx. minutes with a homogenizing unit with rotor stator principle (ultraturrax) before the medium tack silicone-based adhesive in the form of a mixture in n-heptane having a solids content of 73% by weight was added to the mixing vessel.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 100 g/m$^2$. The dried film was then laminated with a backing layer (polyethylenterephthalate (PET) foil 19 µm) to provide the solifenacin-containing self-adhesive layer structure.

Preparation of the TTS

See Examples 1a, 1b.

Example 3

Coating Composition

The formulation of the solifenacin base-containing coating composition is summarized below.

TABLE 3

| | Ex. 3 | |
|---|---|---|
| Ingredient (Trade Name) | Amt [g] | Solids [%] |
| Solifenacin base | 2.5 | 15 |
| Polyvinylpyrrolidone-vinylacetate-copolymer (PVP VA 64 from BASF SE) | 0.2 | 1.5 |
| Polyacrylate adhesive in ethylacetate Solids content of 39% by weight (DURO-TAK 87-4287 from Henkel) | 17.8 | 41.75 |
| Polysiloxane-based PSA in n-heptane Solids content of 73% by weight (BIO-PSA 7-4201 from Dow Corning Healthcare) | 9.5 | 41.75 |
| Total | 30.0 | 100.0 |
| Area Weight [g/m$^2$] | 90 | |
| Loading API [µg/cm$^2$] | 1350 | |

Preparation of the Coating Composition

The polyacrylate adhesive in the form of a solution in ethylacetate having a solids content of 39% by weight was added to a suitable mixing vessel. The polyvinylpyrrolidone-vinylacetate-copolymer was added under stirring. The solifenacin base was subsequently added to the mixing vessel under stirring and the mixture was stirred for approx. 2 hours. The silicone-based adhesive in the form of a mixture in n-heptane was subsequently added and the mixture was stirred for approx. 2 hours to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m$^2$. The dried film was then laminated with a backing layer (polyethylenterephthalate (PET) foil 19 µm) to provide the solifenacin-containing self-adhesive layer structure.

Preparation of the TTS

See Examples 1a, 1b.

Example 4

Coating Composition

The formulation of the solifenacin base-containing coating composition is summarized below.

TABLE 4

| | Ex. 4 | |
|---|---|---|
| Ingredient (Trade Name) | Amt [g] | Solids [%] |
| Solifenacin base | 4.5 | 30 |
| Polyacrylate adhesive in ethylacetate Solids content of 51% by weight (DURO-TAK 387-2051 from Henkel) | 20.5 | 70 |
| Total | 25.0 | 100.0 |
| Area Weight [g/m$^2$] | 95.6 | |
| Loading API [µg/cm$^2$] | 2868 | |

Preparation of the Coating Composition

The polyacrylate adhesive in the form of a solution in ethyl acetate having a solids content of 51% by weight was added to a suitable mixing vessel. The solifenacin base was subsequently added to the mixing vessel under stirring and the mixture was stirred for approx. 1 hour to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/M$^2$. The dried film was then laminated with a backing layer (polyethylentereptalate (PET) foil 19 µm) to provide the solifenacin-containing self-adhesive layer structure.

Preparation of the TTS

See Examples 1a, 1b.

Example 5

Coating Compositions

The formulations of the solifenacin-containing coating composition and the active agent-free coating composition for the skin contact layer are summarized below.

TABLE 5

| | Ex. 5 API-containing composition | |
|---|---|---|
| Ingredient (Trade Name) | Amt [g] | Solids [%] |
| Solifenacin base | 2.30 | 15 |
| Rivastigmine base | 3.82 | 25.5 |
| Tocopherol | 0.127 | 0.085 |
| Polyacrylate adhesive in ethylacetate Solids content of 36.5% by weight (DURO-TAK 87-2353 from Henkel) | 17.41 | 42.415 |
| Polybutylmethacrylate, methyl methacrylate (Plastoid B from Evonic nutrition and care GmbH) | 2.54 | 17 |
| Ethylacetate | 4.50 | — |
| Total | 30.7 | 100.0 |
| Area Weight [g/m$^2$] | 64.2 | |
| Loading Solifenacin base [µg/cm$^2$] | 963 | |

TABLE 5-continued

|  | API free coating composition for the skin contact layer | |
|---|---|---|
|  | Amt [g] | Solids [%] |
| Polysiloxane-based PSA in ethylacetate Solids content of 60% by weight (BIO-PSA 7-4302 from Dow Corning Healthcare) | 29.67 | 98.9 |
| Silicone oil 12500 cST | 0.18 | 1.0 |
| Tocopherol | 0.02 | 0.1 |
| Ethylacetate | 0.13 | — |
| Total | 30.0 | 100.0 |
| Area Weight [g/m²] |  | 30 |

Preparation of the API-Containing Coating Composition

The polyacrylate adhesive in the form of a solution in ethyl acetate having a solids content of 36.5% by weight, the polybutylmethacrylate, methylmethacrylate, the tocopherol, the rivastigmine base and ethylacetate were added to a suitable mixing vessel and the mixture was stirred until a homogeneous solution is formed. The solifenacin base was subsequently added to the mixing vessel and the mixture was stirred for approx. 1 hour to provide the solifenacin-containing coating composition comprising solifenacin and rivastigmine.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 60 g/m². The dried film was then laminated with a backing layer (polyethylenterephthalate (PET) foil 19 µm).

Coating of the API Free Coating Composition (Skin Contact Layer) and Lamination

The active agent-free coating composition was coated on an abhesively equipped foil using hand over knife lab coating equipment (erichson coater).

The coating thickness was chosen such that removal of the solvents results in a area weight of the matrix layer of approx. 30 g/m².

The dried film was then laminated with the solifenacin-containing matrix layer. For this purpose, the abhesively equipped foil used for the coating and drying of the solifenacin-containing matrix layer that was then laminated with a backing layer was removed and the coated and dried skin contact layer was laminated with that film to provide the solifenacin-containing self-adhesive layer structure.

Preparation of the TTS

See Examples 1a, 1b.

Comparative Example A

Coating Composition

The formulation of the solifenacin base-containing coating composition is summarized below.

TABLE 6

|  | Comp. ex. A | |
|---|---|---|
| Ingredient (Trade Name) | Amt [g] | Solids [%] |
| Solifenacin base | 1.5 | 15 |
| Tartaric acid | 0.7 | 7 |
| Polyacrylate adhesive in ethylacetate Solids content of 39% by weight (DURO-TAK 87-4287 from Henkel) | 20.0 | 78 |
| Ethanol anhydrous | 3.0 | — |
| Total | 25.2 | 100.0 |
| Area Weight [g/m²] |  | 88.5 |
| Loading API [µg/cm²] |  | 1328 |

Preparation of the Coating Composition

In a suitable mixing vessel, the tartaric acid was dissolved in ethanol. The solifenacin base was added to the mixing vessel and the mixture was stirred until all components are dissolved. Subsequently, the polyacrylate adhesive in the form of a solution in ethylacetate having a solids content of 39% by weight was added to the mixing vessel and the mixture was stirred for approx. 2 hours.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m². The dried film was then laminated with a backing layer (polyethylenterephthalate (PET) foil 19 µm) to provide the solifenacin-containing self-adhesive layer structure.

Preparation of the TTS

See Examples 1a, 1b.

Comparative Example B

Coating Composition

The formulation of the solifenacin base-containing coating composition is summarized below.

TABLE 7

|  | Comp. ex. A | |
|---|---|---|
| Ingredient (Trade Name) | Amt [g] | Solids [%] |
| Solifenacin base | 0.9 | 5 |
| Isopropylmyristate | 0.5 | 2.5 |
| Polysiloxane-based PSA in n-heptane Solids content of 73% by weight (BIO-PSA 7-4201 from Dow Corning Healthcare) | 23.6 | 92.5 |
| Total | 25.0 | 100.0 |

Preparation of the Coating Composition

The polysiloxane-based adhesive in the form of a mixture in n-heptane having a solids content of 73% by weight was added to a suitable mixing vessel. The isopropylmyristate and the solifenacin base were subsequently added to the mixing vessel under stirring and the mixture was stirred for approx. 2 hours.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

Due to the poor processability of the coating composition a uniform coating could not be achieved when it was aimed at an area weight of 90 g/m². A dried matrix layer with an area weight 67.8 g/m² could be obtained that showed intense streaking/striation. A permeation study was not performed with Comparative example B.

Example 6

Coating Composition

The formulation of the solifenacin base-containing coating composition is summarized below.

TABLE 8

| Ingredient (Trade Name) | Ex. 6 | |
|---|---|---|
| | Amt [g] | Solids [%] |
| Solifenacin base | 2.4 | 30 |
| Polyacrylate adhesive in ethylacetate Solids content of 39% by weight (DURO-TAK 87-4287 from Henkel) | 15.0 | 70 |
| Total | 17.4 | 100.0 |
| Area Weight [g/m²] | 95.3 | |
| Loading API [µg/cm²] | 2859 | |

Preparation of the Coating Composition

The polyacrylate adhesive in the form of a solution in ethyl acetate having a solids content of 39% by weight was added to a suitable mixing vessel. The solifenacin base was subsequently added to the mixing vessel under stirring and the mixture was stirred for approx. 1 hour to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m². The dried film was then laminated with a backing layer (polyethylenterephthalate (PET) foil 19 µm) to provide the solifenacin-containing self-adhesive layer structure.

Preparation of the TTS

See Examples 1a, 1b.

Example 7

Coating Composition

The formulation of the solifenacin base-containing coating composition is summarized below.

TABLE 9

| Ingredient (Trade Name) | Ex. 7 | |
|---|---|---|
| | Amt [g] | Solids [%] |
| Solifenacin base | 0.7 | 5 |
| Polyisobutylene adhesive in hexane Solids content of 60% by weight PIB B10/B100 (15%/85%) from BASF SE | 20.6 | 95 |
| Total | 21.3 | 100.0 |
| Area Weight [g/m²] | 129.5 | |
| Loading API [µg/cm²] | 648 | |

Preparation of the Coating Composition

The polyisobutylene adhesive in the form of a solution in hexane having a solids content of 60% by weight was added to a suitable mixing vessel. The solifenacin base was subsequently added to the mixing vessel under stirring and the mixture was stirred for approx. 1 hour to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 130 g/m². The dried film was then laminated with a backing layer (polyethylenterephthalate (PET) foil 19 µm) to provide the solifenacin-containing self-adhesive layer structure.

Preparation of the TTS

See Examples 1a, 1b.

Example 8

Coating Composition

The formulation of the solifenacin base-containing coating composition is summarized below.

TABLE 10

| Ingredient (Trade Name) | Ex. 8 | |
|---|---|---|
| | Amt [g] | Solids [%] |
| Solifenacin base | 1.5 | 15 |
| Lauryl alcohol | 1.5 | 15 |
| Ethanol | 3.0 | — |
| Polyacrylate adhesive in ethylacetate Solids content of 39% by weight (DURO-TAK 87-4287 from Henkel) | 17.9 | 70 |
| Total | 23.9 | 100.0 |
| Area Weight [g/m²] | 101.5 | |
| Loading API [µg/cm²] | 1523 | |

Preparation of the Coating Composition

In a suitable mixing vessel, the solifenacin base was suspended in lauryl alcohol and ethanol and stirred until complete dissolution of solifenacin base. Subsequently, the polyacrylate adhesive in the form of a solution in ethylacetate having a solids content of 39% by weight was added to the mixing vessel and the mixture was stirred for approx. 2 hours to provide the solifenacin-containing coating composition.

Coating of the Coating Composition

The solifenacin-containing coating composition was coated within 24 hours on a abhesively equipped foil (Scotchpak 1022 from 3M which may function as a release liner) using hand over knife lab coating equipment (Erichsen coater).

The coating thickness was chosen such that removal of the solvents results in a area weight of the matrix layer of approx. 100 g/m². The dried film was then laminated with a backing layer (polyethylenterephthalate (PET) foil 19 μm) to provide the solifenacin-containing self-adhesive layer structure.

Preparation of the TTS

See Examples 1a, 1b.

Example 9

Coating Composition

The formulation of the solifenacin base-containing coating composition is summarized below.

TABLE 11

| Ingredient (Trade Name) | Ex. 9 Amt [g] | Solids [%] |
| --- | --- | --- |
| Solifenacin base | 0.9 | 5 |
| Pentyl acetate | 1.8 | 10 |
| Ethanol | 1.0 | — |
| Polysiloxane-based PSA in n-heptane Solids content of 73% by weight (BIO-PSA 7-4201 from Dow Corning Healthcare) | 21.3 | 85 |
| Total | 25.1 | 100.0 |
| Area Weight [g/m²] | 86.5 | |
| Loading API [μg/cm²] | 433 | |

Preparation of the Coating Composition

In a suitable mixing vessel, the solifenacin base was suspended in pentyl acetate and ethanol and stirred until complete dissolution of the solifenacin base. The polysiloxane-based adhesive in the form of a mixture in n-heptane having a solids content of 73% by weight was added. The mixture was stirred for approx. 1 hour until homogeneous to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m². The dried film was then laminated with a backing layer (polyethylenterephthalate (PET) foil 19 μm) to provide the solifenacin-containing self-adhesive layer structure.

Preparation of the TTS

See Examples 1a, 1b.

Example 10

Coating Composition

The formulation of the solifenacin base-containing coating composition is summarized below.

TABLE 12

| Ingredient (Trade Name) | Ex. 10 Amt [g] | Solids [%] |
| --- | --- | --- |
| Solifenacin base | 0.9 | 5 |
| Oleic acid | 1.8 | 10 |
| Ethanol | 0.9 | — |
| Polysiloxane-based PSA in n-heptane Solids content of 73% by weight (BIO-PSA 7-4201 from Dow Corning Healthcare) | 21.3 | 85 |
| Total | 25.0 | 100.0 |
| Area Weight [g/m²] | 87.7 | |
| Loading API [μg/cm²] | 439 | |

Preparation of the Coating Composition

In a suitable mixing vessel, the solifenacin base was suspended in oleic acid and ethanol and stirred until complete dissolution of the solifenacin base. The polysiloxane-based adhesive in the form of a mixture in n-heptane having a solids content of 73% by weight was added. The mixture was stirred for approx. 1 hour until homogeneous to provide the solifenacin-containing coating composition.

Coating of the Coating Composition

The solifenacin-containing coating composition was coated within 24 hours on a abhesively equipped foil (Scotchpak 1022 from 3M, which may function as a release liner) using hand over knife lab coating equipment (Erichsen coater).

The coating thickness was chosen such that removal of the solvents results in a area weight of the matrix layer of approx. 90 g/m². The dried film was then laminated with a backing layer (polyethylenterephthalate (PET) foil 19 μm) to provide the solifenacin-containing self-adhesive layer structure.

Preparation of the TTS

See Examples 1a, 1b.

Example 11

Measurement of Skin Permeation

The permeated amount of solifenacin and the corresponding skin permeation rates of TTS prepared according to Example 1a, Example 1b, Example 2a, Example 2b, Example 3, Example 4, Example 5 and Comparative example A were determined by in vitro experiments in accordance with the OECD Guideline (adopted Apr. 13, 2004) carried out with a 9.0 ml Franz diffusion cell. Split thickness human skin from cosmetic surgeries (female abdomen, date of birth 1963) was used. A dermatone was used to prepare skin to a thickness of 500 μm, with an intact epidermis for all TTS. Die cuts with an area of 1.188 cm² were punched from the TTS. The permeated amount of solifenacin in the receptor medium of the Franz diffusion cell (phosphate buffer solution pH 5.5 with 0.1% saline azide as antibacteriological agent) at a temperature of 32±1° C. was measured and the corresponding cumulative permeated amount and the skin permeation rate were calculated.

The results are shown in Tables 13 to 16 below and in FIGS. 1a to 2b.

TABLE 13

| | Permeated amount with SD [µg/cm²] | | | | | | | |
|---|---|---|---|---|---|---|---|---|
| Elapsed | Ex. 1a (n = 3) | | Ex. 1b (n = 3) | | Ex. 2a (n = 3) | | Ex. 2b (n = 3) | |
| time [h] | Amount | SD | Amount | SD | Amount | SD | Amount | SD |
| 0 | 0 | 0 | 0 | 0 | 0 | 0 | 0 | 0 |
| 8 | 29.9 | 5.8 | 65.2 | 2.8 | 167.7 | 60.5 | 95.7 | 29.0 |
| 24 | 128.3 | 28.6 | 150.3 | 3.5 | 263.0 | 23.5 | 263.3 | 36.1 |
| 32 | 65.0 | 22.3 | 64.9 | 2.4 | 107.0 | 6.6 | 125.3 | 11.6 |
| 48 | 69.1 | 4.2 | 71.5 | 4.8 | 152.7 | 4.7 | 193.0 | 5.6 |
| 72 | 61.2 | 3.7 | 48.4 | 2.6 | 143.0 | 12.5 | 203.0 | 33.2 |
| Cum. at 72 h | 353.7 | 46.1 | 400.3 | 13.7 | 833.3 | 72.7 | 879.3 | 49.2 |

| | Permeated amount with SD [µg/cm²] | | | | | | | |
|---|---|---|---|---|---|---|---|---|
| Elapsed | Ex. 3 (n = 3) | | Ex. 4 (n = 3) | | Ex. 5 (n = 3) | | Comp. ex. A (n = 3) | |
| time [h] | Amount | SD | Amount | SD | Amount | SD | Amount | SD |
| 0 | 0 | 0 | 0 | 0 | 0 | 0 | 0 | 0 |
| 8 | 132.7 | 14.5 | 70.9 | 16.3 | 83.2 | 6.5 | 0 | 0 |
| 24 | 294.0 | 8.7 | 236.3 | 31.6 | 172.7 | 2.5 | 2.3 | 0.2 |
| 32 | 140.3 | 10.2 | 113.7 | 13.6 | 65.4 | 2.4 | 2.4 | 0.1 |
| 48 | 209.7 | 13.4 | 172.0 | 18.4 | 78.1 | 1.9 | 5.5 | 0.8 |
| 72 | 224.3 | 6.5 | 204.7 | 20.6 | 74.7 | 1.8 | 9.4 | 1.3 |
| Cum. at 72 h | 1001.3 | 26.1 | 797.7 | 100.8 | 474.0 | 7.5 | 19.6 | 2.5 |

TABLE 14

| | Skin permeation rate with SD [µg/cm²-hr] | | | | | | | |
|---|---|---|---|---|---|---|---|---|
| Elapsed | Ex. 1a (n = 3) | | Ex. 1b (n = 3) | | Ex. 2a (n = 3) | | Ex. 2b (n = 3) | |
| time [h] | Rate | SD | Rate | SD | Rate | SD | Rate | SD |
| 0 | 0 | 0 | 0 | 0 | 0 | 0 | 0 | 0 |
| 8 | 3.7 | 0.7 | 8.2 | 0.4 | 21.0 | 7.6 | 12.0 | 3.6 |
| 24 | 8.0 | 1.3 | 9.4 | 0.2 | 16.4 | 1.5 | 16.5 | 2.3 |
| 32 | 8.1 | 2.8 | 8.1 | 0.3 | 13.4 | 0.8 | 15.7 | 1.5 |
| 48 | 4.3 | 0.3 | 4.5 | 0.3 | 9.5 | 0.3 | 12.1 | 0.4 |
| 72 | 2.6 | 0.2 | 2.0 | 0.1 | 6.0 | 0.5 | 8.5 | 1.4 |

| | Skin permeation rate with SD [µg/cm²-hr] | | | | | | | |
|---|---|---|---|---|---|---|---|---|
| Elapsed | Ex. 3 (n = 3) | | Ex. 4 (n = 3) | | Ex. 5 (n = 3) | | Comp. ex. A (n = 3) | |
| time [h] | Rate | SD | Rate | SD | Rate | SD | Rate | SD |
| 0 | 0 | 0 | 0 | 0 | 0 | 0 | 0 | 0 |
| 8 | 16.6 | 1.8 | 8.9 | 2.0 | 10.4 | 0.8 | 0 | 0 |
| 24 | 18.4 | 0.5 | 14.7 | 2.0 | 10.8 | 0.2 | 0.1 | 0.0 |
| 32 | 17.5 | 1.3 | 14.2 | 1.7 | 8.2 | 0.3 | 0.3 | 0.0 |
| 48 | 13.1 | 0.8 | 10.8 | 1.2 | 4.9 | 0.1 | 0.3 | 0.1 |
| 72 | 9.3 | 0.3 | 8.5 | 0.9 | 3.1 | 0.1 | 0.4 | 0.1 |

TABLE 15

| Cumulative skin permeation rate [µg/cm²-hr] over 72 hours | | | | | | | |
|---|---|---|---|---|---|---|---|
| Ex. 1a | Ex. 1b | Ex. 2a | Ex. 2b | Ex. 3 | Ex. 4 | Ex. 5 | Comp. ex. A |
| 4.9 | 5.6 | 11.6 | 12.2 | 13.9 | 11.1 | 6.6 | 0.3 |

TABLE 16

| Ratio Cumulative permeated amount at 72 hours/API Loading * 100 (Active agent utilization) | | | | | | | |
|---|---|---|---|---|---|---|---|
| Ex. 1a | Ex. 1b | Ex. 2a | Ex. 2b | Ex. 3 | Ex. 4 | Ex. 5 | Comp. ex. A |
| 75.6% | 85.8% | 81.4% | 91.6% | 74.1% | 27.8% | 49.2% | 1.5% |

Example 12

Measurement of Skin Permeation

The permeated amount of solifenacin and the corresponding skin permeation rates of TTS prepared according to Example 6, Example 7, Example 8, Example 9 and Example 10 were determined by in vitro experiments in accordance with the OECD Guideline (adopted Apr. 13, 2004) carried out with a 9.0 ml Franz diffusion cell. Split thickness human skin from cosmetic surgeries (female abdomen, date of birth 1958) was used. A dermatone was used to prepare skin to a thickness of 500 μm, with an intact epidermis for all TTS. Die cuts with an area of 1.188 $cm^2$ were punched from the TTS. The permeated amount of solifenacin in the receptor medium of the Franz diffusion cell (phosphate buffer solution pH5.5 with 0.1% saline azide as antibacteriological agent) at a temperature of 32±1° C. was measured and the corresponding cumulative permeated amount and the skin permeation rate were calculated.

Figure 3A:
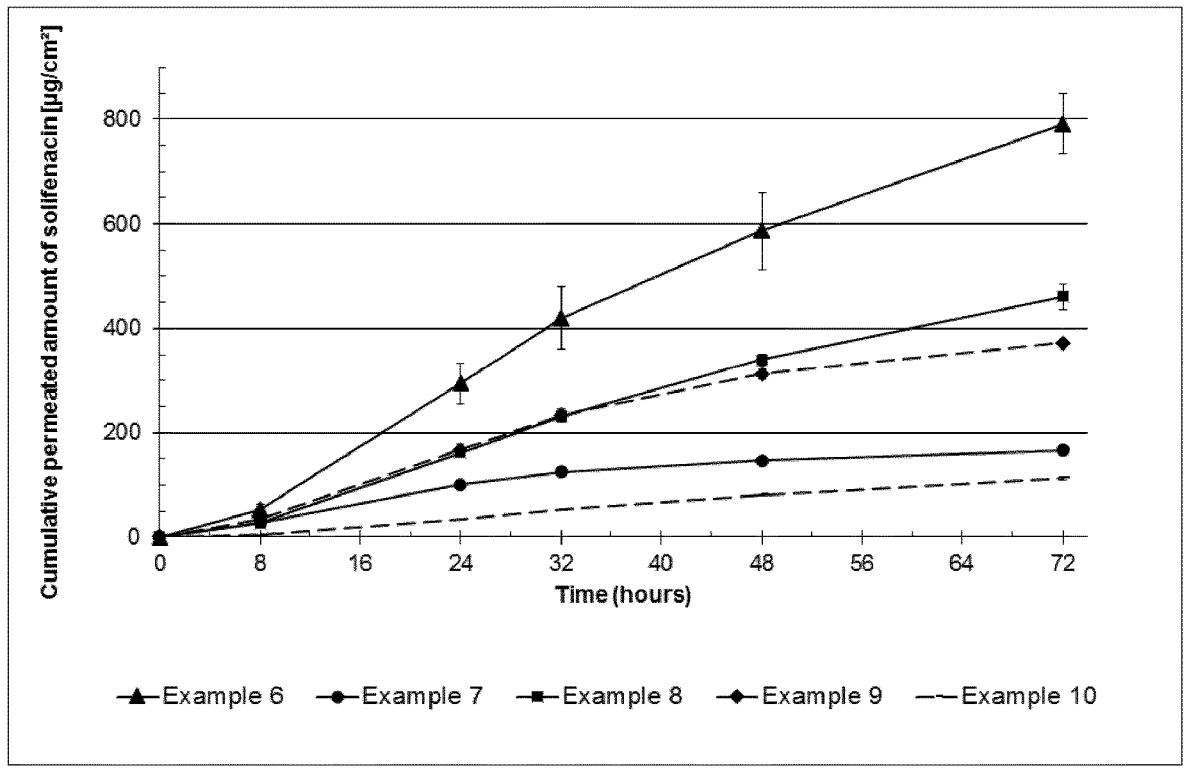
FIG. 3a depicts the cumulative permeated amount of solifenacin of Example 6, Example 7, Example 8, Example 9 and Example 10 over a time interval of 72 hours.
Figure 3B:
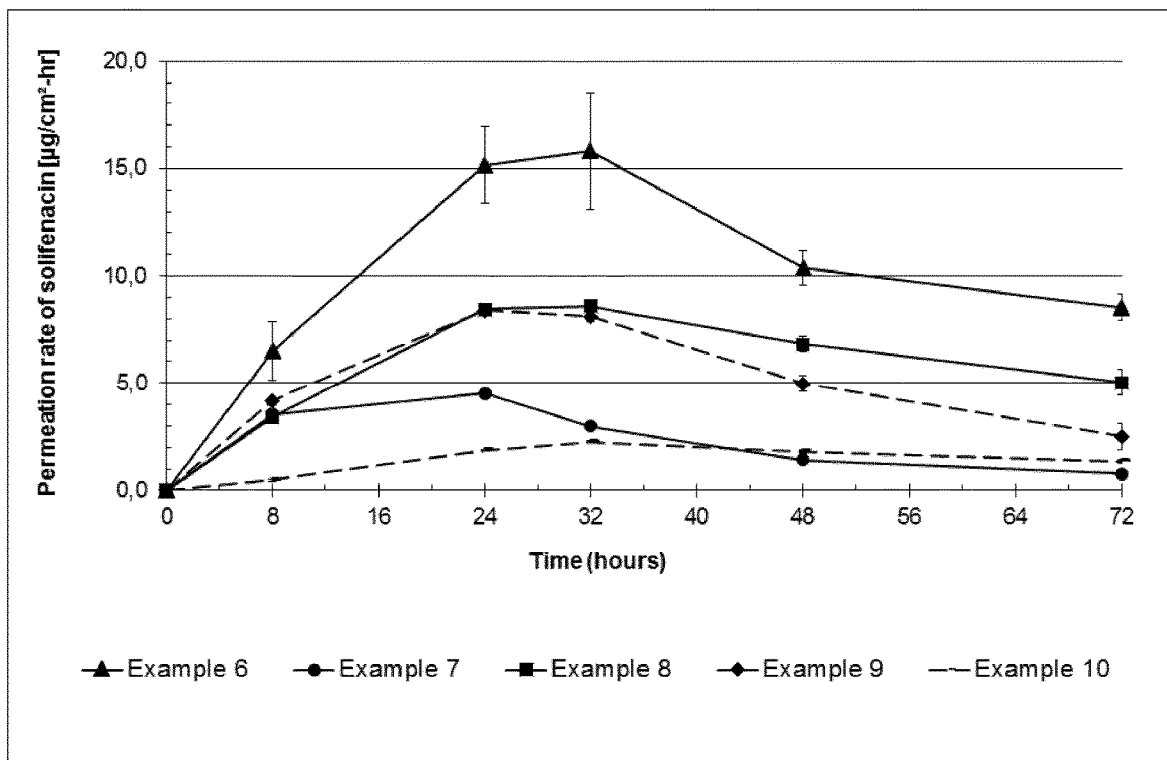
FIG. 3b depicts the skin permeation rate of Example 6, Example 7, Example 8, Example 9 and Example 10 over a time interval of 72 hours.

The results are shown in Tables 17 to 20 below and in FIGS. 3a and 3b.

TABLE 17

| Permeated amount with SD [μg/$cm^2$] | | | | | | |
|---|---|---|---|---|---|---|
| Elapsed | Ex. 6 (n = 3) | | Ex. 7 (n = 3) | | Ex. 8 (n = 3) | |
| time [h] | Amount | SD | Amount | SD | Amount | SD |
| 0 | 0 | 0 | 0 | 0 | 0 | 0 |
| 8 | 51.9 | 10.9 | 28.4 | 1.3 | 27.3 | 1.4 |
| 24 | 242.3 | 28.5 | 72.3 | 0.8 | 135.0 | 3.5 |
| 32 | 126.3 | 21.8 | 23.8 | 0.6 | 68.6 | 2.0 |
| 48 | 166.0 | 13.0 | 22.8 | 1.1 | 109.3 | 5.8 |
| 72 | 204.7 | 15.0 | 18.7 | 1.8 | 121.0 | 14.7 |
| Cum. at 72 h | 791.0 | 58.0 | 166.0 | 3.6 | 461.0 | 23.6 |

| Permeated amount with SD [μg/$cm^2$] | | | | |
|---|---|---|---|---|
| Elapsed | Ex. 9 (n = 3) | | Ex. 10 (n = 3) | |
| time [h] | Amount | SD | Amount | SD |
| 0 | 0 | 0 | 0 | 0 |
| 8 | 33.5 | 3.9 | 3.9 | 0.4 |
| 24 | 134.3 | 7.5 | 29.8 | 0.1 |
| 32 | 65.0 | 1.0 | 18.1 | 0.3 |
| 48 | 79.8 | 3.0 | 28.8 | 1.3 |
| 72 | 60.2 | 3.1 | 32.6 | 2.0 |
| Cum. at 72 h | 372.7 | 6.4 | 113.3 | 3.5 |

TABLE 18

| Skin permeation rate with SD [μg/$cm^2$-hr] | | | | | | |
|---|---|---|---|---|---|---|
| Elapsed | Ex. 6 (n = 3) | | Ex. 7 (n = 3) | | Ex. 8 (n = 3) | |
| time [h] | Rate | SD | Rate | SD | Rate | SD |
| 0 | 0 | 0 | 0 | 0 | 0 | 0 |
| 8 | 6.5 | 1.4 | 3.5 | 0.2 | 3.4 | 0.2 |
| 24 | 15.2 | 1.8 | 4.5 | 0.0 | 8.4 | 0.2 |
| 32 | 15.8 | 2.7 | 3.0 | 0.1 | 8.6 | 0.3 |
| 48 | 10.4 | 0.8 | 1.4 | 0.1 | 6.8 | 0.4 |
| 72 | 8.5 | 0.6 | 0.8 | 0.1 | 5.0 | 0.6 |

| Skin permeation rate with SD [μg/$cm^2$-hr] | | | | |
|---|---|---|---|---|
| Elapsed | Ex. 9 (n = 3) | | Ex. 10 (n = 3) | |
| time [h] | Rate | SD | Rate | SD |
| 0 | 0 | 0 | 0 | 0 |
| 8 | 4.2 | 0.5 | 0.5 | 0.1 |
| 24 | 8.4 | 0.5 | 1.9 | 0.0 |
| 32 | 8.1 | 0.1 | 2.3 | 0.0 |
| 48 | 5.0 | 0.2 | 1.8 | 0.1 |
| 72 | 2.5 | 0.1 | 1.4 | 0.1 |

TABLE 19

| Cumulative skin permeation rate [μg/$cm^2$-hr] over 72 hours | | | | |
|---|---|---|---|---|
| Ex. 6 | Ex. 7 | Ex. 8 | Ex. 9 | Ex. 10 |
| 11.0 | 2.3 | 6.4 | 5.2 | 1.6 |

TABLE 20

| Ratio Cumulative permeated amount at 72 hours/API Loading * 100 (Active agent utilization) | | | | |
|---|---|---|---|---|
| Ex. 6 | Ex. 7 | Ex. 8 | Ex. 9 | Ex. 10 |
| 27.7% | 25.6% | 30.3% | 86.1% | 25.7% |

The Invention Relates in Particular to the Following Further Items

1. A transdermal therapeutic system for the transdermal administration of solifenacin comprising a solifenacin-containing layer structure,
   the solifenacin-containing layer structure comprising:
   A) a backing layer, and
   B) a solifenacin-containing layer comprising a therapeutically effective amount of solifenacin,
   wherein the solifenacin-containing layer structure comprises at least one polymer, and
   wherein the transdermal therapeutic system does not contain a transdermal permeation enhancer selected from the group consisting of a fatty acid ester, a terpene, and a carboxylic acid having 2 to 10 carbon atoms.
2. The transdermal therapeutic system according to item 1,
   wherein the transdermal therapeutic system does not contain a transdermal permeation enhancer selected from the group consisting of a fatty acid ester, a terpene, and a carboxylic acid.

3. The transdermal therapeutic system according to item 1,
wherein the transdermal therapeutic system does not contain a transdermal permeation enhancer.
4. The transdermal therapeutic system according to any one of items 1 to 3,
wherein the solifenacin-containing layer structure is self-adhesive.
5. The transdermal therapeutic system according to any one of items 1 to 4, wherein the at least one polymer is selected from the group consisting of a polymer based on polysiloxanes, a silicone acrylic hybrid polymer, a polymer based on polyisobutylenes, a styrene-isoprene-styrene block copolymer, and an acrylate polymer.
6. The transdermal therapeutic system according to any one of items 1 to 5, wherein the at least one polymer is selected from the group consisting of a polymer based on polysiloxanes, a silicone acrylic hybrid polymer, a polymer based on polyisobutylenes, and an acrylate polymer, preferably the at least one polymer is selected from the group consisting of a polymer based on polysiloxanes and a silicone acrylic hybrid polymer.
7. The transdermal therapeutic system according to any one of items 1 to 6, wherein the at least one polymer is contained in the solifenacin-containing layer.
8. The transdermal therapeutic system according to any one of items 1 to 7, wherein the at least one polymer is contained in the solifenacin-containing layer in an amount of from about 20% to about 99% by weight, preferably of from about 30% to about 99% by weight, more preferably of from about 40% to about 99% by weight based on the solifenacin-containing layer.
9. The transdermal therapeutic system according to any one of items 1 to 8,
wherein the total amount of polymer contained in the solifenacin-containing layer ranges from about 40% to about 99% by weight, preferably from about 50% to about 99% by weight, more preferably from about 60% to about 99% by weight based on the solifenacin-containing layer.
10. The transdermal therapeutic system according to any one of items 1 to 9, wherein the solifenacin-containing layer comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer.
11. The transdermal therapeutic system according to any one of items 1 to 10, wherein the solifenacin-containing layer comprises a blend of at least two polymers based on polysiloxanes which are characterized by different physical properties.
12. The transdermal therapeutic system according to any one of items 1 to 10, wherein the solifenacin-containing layer comprises a blend of a polymer based on polysiloxanes and an acrylate polymer.
13. The transdermal therapeutic system according to any one of items 1 to 10, wherein the solifenacin-containing layer comprises a blend of at least two silicone acrylic hybrid polymers which are characterized by different physical properties.
14. The transdermal therapeutic system according to any one of items 1 to 10, wherein the solifenacin-containing layer comprises a blend of a silicone acrylic hybrid polymer and a polymer based on polysiloxanes.
15. The transdermal therapeutic system according to any one of items 1 to 10, wherein the solifenacin-containing layer comprises a blend of a silicone acrylic hybrid polymer and an acrylate polymer.
16. The transdermal therapeutic system according to any one of items 1 to 10, wherein the solifenacin-containing layer comprises a blend of at least two polyisobutylenes which are characterized by different physical properties.
17. The transdermal therapeutic system according to any one of items 1 to 16, wherein the solifenacin-containing layer is a solifenacin-containing matrix layer.
18. The transdermal therapeutic system according to any one of items 1 to 17, wherein the area weight of the solifenacin-containing layer ranges from about 20 to about 160 $g/m^2$.
19. The transdermal therapeutic system according to any one of items 1 to 18, wherein the area weight of the solifenacin-containing layer ranges from about 40 to about 150 $g/m^2$.
20. The transdermal therapeutic system according to any one of items 1 to 19, wherein the area weight of the solifenacin-containing layer ranges from about 50 to about 140 $g/m^2$.
21. The transdermal therapeutic system according to any one of items 1 to 20, wherein the solifenacin-containing layer represents the skin contact layer.
22. The transdermal therapeutic system according to any one of items 1 to 20, wherein the solifenacin-containing layer structure comprises an additional skin contact layer, which comprises the at least one polymer.
23. The transdermal therapeutic system according to any one of items 1 to 20, wherein the solifenacin-containing layer structure comprises an additional skin contact layer and both the solifenacin-containing layer and the skin contact layer comprise at least one polymer.
24. The transdermal therapeutic system according to item 22 or 23, wherein the at least one polymer in the skin contact layer is contained in an amount of from about 20% to about 100% by weight, preferably of from about 30% to about 100% by weight, more preferably of from about 40% to about 100% by weight based on the skin contact layer.
25. The transdermal therapeutic system according to any one of items 22 to 24,
wherein the total amount of polymer contained in the skin contact layer ranges from about 40% to about 100% by weight, preferably from about 50% to about 100% by weight, more preferably from about 60% to about 100% by weight based on the skin contact layer.
26. The transdermal therapeutic system according to any one of items 22 to 25, wherein the skin contact layer comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer.
27. The transdermal therapeutic system according to any one of items 22 to 26, wherein the skin contact layer comprises a blend of at least two polymers based on polysiloxanes which are characterized by different physical properties.
28. The transdermal therapeutic system according to any one of items 22 to 26, wherein the skin contact layer comprises a blend of a polymer based on polysiloxanes and an acrylate polymer.

29. The transdermal therapeutic system according to any one of items 22 to 26, wherein the skin contact layer comprises a blend of at least two silicone acrylic hybrid polymers which are characterized by different physical properties.
30. The transdermal therapeutic system according to any one of items 22 to 26, wherein the skin contact layer comprises a blend of a silicone acrylic hybrid polymer and a polymer based on polysiloxanes.
31. The transdermal therapeutic system according to any one of items 22 to 26, wherein the skin contact layer comprises a blend of a silicone acrylic hybrid polymer and an acrylate polymer.
32. The transdermal therapeutic system according to any one of items 22 to 26, wherein the skin contact layer comprises a blend of at least two polyisobutylenes which are characterized by different physical properties.
33. The transdermal therapeutic system according to any one of items 22 to 32, wherein the skin contact layer is a self-adhesive matrix layer.
34. The transdermal therapeutic system according to any one of items 22 to 33, wherein the area weight of the skin contact layer ranges from about 10 to about 160 g/m².
35. The transdermal therapeutic system according to any one of items 22 to 34, wherein the area weight of the skin contact layer ranges from about 10 to about 100 g/m².
36. The transdermal therapeutic system according to any one of items 22 to 35, wherein the area weight of the skin contact layer ranges from about 10 to about 60 g/m².
37. The transdermal therapeutic system according to any one of items 1 to 36, wherein the solifenacin-containing layer structure comprises at least one polymer based on polysiloxanes.
38. Transdermal therapeutic system according to item 37, wherein the polymer based on polysiloxanes is obtainable by polycondensation of silanol endblocked polydimethylsiloxane with a silicate resin.
39. Transdermal therapeutic system according to item 37 or 38, wherein the polymer based on polysiloxanes is a pressure-sensitive adhesive based on polysiloxanes.
40. The transdermal therapeutic system according to any one of items 37 to 39,
wherein the pressure-sensitive adhesive based on polysiloxanes is characterized by a solution viscosity at 25° C. and about 60% solids content in n-heptane of more than about 150 mPa s, preferably as measured using a Brookfield RVT viscometer equipped with a spindle number 5 at 50 RPM.
41. The transdermal therapeutic system according to any one of items 37 to 40,
wherein the pressure-sensitive adhesive based on polysiloxanes is characterized by a solution viscosity at 25° C. and about 60% solids content in n-heptane of from about 200 mPa s to about 700 mPa s, preferably as measured using a Brookfield RVT viscometer equipped with a spindle number 5 at 50 RPM.
42. The transdermal therapeutic system according to any one of items 37 to 41,
wherein the pressure-sensitive adhesive based on polysiloxanes is characterized by a solution viscosity at 25° C. and about 60% solids content in heptane of about 450 mPa s or of about 500 mPa s, preferably as measured using a Brookfield RVT viscometer equipped with a spindle number 5 at 50 RPM.
43. The transdermal therapeutic system according to any one of items 37 to 42,
wherein the pressure-sensitive adhesive based on polysiloxanes is characterized by a complex viscosity at 0.01 rad/s at 30° C. of less than about $1 \times 10^9$ Poise, preferably as measured using a Rheometrics ARES rheometer, wherein the rheometer is equipped with 8 mm plates and the gap zeroed.
44. The transdermal therapeutic system according to any one of items 37 to 43,
wherein the pressure-sensitive adhesive based on polysiloxanes is characterized by a complex viscosity at 0.01 rad/s at 30° C. of from about $1 \times 10^5$ to about $9 \times 10^8$ Poise, preferably as measured using a Rheometrics ARES rheometer, wherein the rheometer is equipped with 8 mm plates and the gap zeroed.
45. The transdermal therapeutic system according to any one of items 37 to 44,
wherein the pressure-sensitive adhesive based on polysiloxanes is characterized by a complex viscosity at 0.01 rad/s at 30° C. of $1 \times 10^8$ Poise, preferably as measured using a Rheometrics ARES rheometer, wherein the rheometer is equipped with 8 mm plates and the gap zeroed.
46. The transdermal therapeutic system according to any one of items 37 to 45,
wherein the pressure-sensitive adhesive based on polysiloxanes is characterized by a complex viscosity at 0.01 rad/s at 30° C. of $5 \times 10^6$ Poise, preferably as measured using a Rheometrics ARES rheometer, wherein the rheometer is equipped with 8 mm plates and the gap zeroed.
47. The transdermal therapeutic system according to any one of items 1 to 46,
wherein the solifenacin-containing layer structure comprises a blend of at least two pressure-sensitive adhesives based on polysiloxanes which are characterized by different solution viscosities and/or by different complex viscosities.
48. The transdermal therapeutic system according to any one of items 1 to 47,
wherein the solifenacin-containing layer structure comprises at least one silicone acrylic hybrid polymer.
49. The transdermal therapeutic system according to item 48,
wherein the silicone acrylic hybrid polymer contains a continuous, silicone external phase and a discontinuous, acrylic internal phase.
50. The transdermal therapeutic system according to item 48,
wherein the silicone acrylic hybrid polymer contains a continuous, acrylic external phase and a discontinuous, silicone internal phase.
51. The transdermal therapeutic system according to any one of items 48 to 50,
wherein the silicone acrylic hybrid polymer is a silicone acrylic hybrid pressure-sensitive adhesive.
52. The transdermal therapeutic system according to any one of items 48 to 51,
wherein the silicone acrylic hybrid pressure-sensitive adhesive has a weight ratio of silicone to acrylate of from 5:95 to 95:5.
53. The transdermal therapeutic system according to any one of items 48 to 52, wherein the silicone acrylic hybrid pressure-sensitive adhesive has a weight ratio of silicone to acrylate of from 40:60 to 60:40.
54. The transdermal therapeutic system according to any one of items 48 to 53,
wherein the silicone acrylic hybrid pressure-sensitive adhesive has a weight ratio of silicone to acrylate of about 50:50.
55. The transdermal therapeutic system according to any one of items 48 to 54,
wherein the silicone acrylic hybrid polymer is obtainable from
 (a) a silicon-containing pressure-sensitive adhesive composition comprising acrylate or methacrylate functionality.
56. The transdermal therapeutic system according to any one of items 48 to 55,
wherein the silicone acrylic hybrid polymer is a silicone acrylic hybrid pressure-sensitive adhesive comprising the reaction product of
 (a) a silicon-containing pressure-sensitive adhesive composition comprising acrylate or methacrylate functionality;
 (b) an ethylenically unsaturated monomer; and
 (c) an initiator.
57. The transdermal therapeutic system according to any one of items 51 to 56,
wherein the silicon-containing pressure-sensitive adhesive composition comprising acrylate or methacrylate functionality is the condensation reaction product of
 (a1) a silicone resin, and
 (a2) a silicone polymer, and
 (a3) a silicon-containing capping agent comprising acrylate or methacrylate functionality.
58. The transdermal therapeutic system according to any one of items 51 to 57,
wherein the silicon-containing pressure-sensitive adhesive composition comprising acrylate or methacrylate functionality is the condensation reaction product of
 (a1) a silicone resin, and
 (a2) a silicone polymer, and
 (a3) a silicon-containing capping agent comprising acrylate or methacrylate functionality, wherein said silicon-containing capping agent is of the general formula $XYR'_bSiZ_{3-b}$, wherein X is a monovalent radical of the general formula AE, where E is —O— or —NH— and A is an acryl group or methacryl group, Y is a divalent alkylene radical having from 1 to 6 carbon atoms, R' is a methyl or a phenyl radical, Z is a monovalent hydrolysable organic radical or halogen, and b is 0 or 1;
 wherein the silicone resin and silicone polymer are reacted to form a pressure-sensitive adhesive, wherein the silicon-containing capping agent is introduced prior to, during, or after the silicone resin and silicone polymer are reacted,
 and wherein the silicon-containing capping agent reacts with the pressure-sensitive adhesive after the silicone resin and silicone polymer have been condensation reacted to form the pressure-sensitive adhesive, or the silicon-containing capping agent reacts in situ with the silicone resin and silicone polymer.
59. The transdermal therapeutic system according to any one of items 56 to 58,
wherein the ethylenically unsaturated monomer is selected from the group consisting of aliphatic acrylates, aliphatic methacrylates, cycloaliphatic acrylates, cycloaliphatic methacrylates, and combinations thereof, each of said compounds having up to 20 carbon atoms in the alkyl radical.
60. The transdermal therapeutic system according to any one of items 56 to 59,
wherein the ethylenically unsaturated monomer is a combination of 2-ethylhexyl acrylate and methyl acrylate.
61. The transdermal therapeutic system according to any one of items 56 to 60,
wherein the ethylenically unsaturated monomer is a combination of 2-ethylhexyl acrylate and methyl acrylate in a ratio of from 40:60 to 70:30, preferably in a ratio of from 65:35 to 55:45 or of from 55:45 to 45:50.
62. The transdermal therapeutic system according to any one of items 56 to 61,
wherein the reaction product of
 (a) the silicon-containing pressure-sensitive adhesive composition comprising acrylate or methacrylate functionality;
 (b) the ethylenically unsaturated monomer; and
 (c) the initiator
contains a continuous, silicone external phase and a discontinuous, acrylic internal phase.
63. The transdermal therapeutic system according to any one of items 56 to 61,
wherein the reaction product of
 (a) the silicon-containing pressure-sensitive adhesive composition comprising acrylate or methacrylate functionality;
 (b) the ethylenically unsaturated monomer; and
 (c) the initiator
contains a continuous, acrylic external phase and a discontinuous, silicone internal phase.
64. The transdermal therapeutic system according to any one of items 48 to 54,
wherein the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.
65. The transdermal therapeutic system according to any one of items 51 to 64,
wherein the silicone acrylic hybrid pressure-sensitive adhesive is characterized by a solution viscosity at 25° C. and about 50% solids content in ethyl acetate of more than about 400 cP, preferably as measured using a Brookfield RVT viscometer equipped with a spindle number 5 at 50 RPM.
66. The transdermal therapeutic system according to any one of items 51 to 65,
wherein the silicone acrylic hybrid pressure-sensitive adhesive is characterized by a solution viscosity at 25° C. and about 50% solids content in ethyl acetate of from about 500 cP to about 3,500 cP, preferably as measured using a Brookfield RVT viscometer equipped with a spindle number 5 at 50 RPM.
67. The transdermal therapeutic system according to any one of items 51 to 66,
wherein the silicone acrylic hybrid pressure-sensitive adhesive is characterized by a solution viscosity at 25° C. and about 50% solids content in ethyl acetate of from about 1,000 cP to about 3,000 cP, preferably as measured using a Brookfield RVT viscometer equipped with a spindle number 5 at 50 RPM.
68. The transdermal therapeutic system according to any one of items 51 to 67, wherein the silicone acrylic hybrid pressure-sensitive adhesive is characterized by a solution viscosity at 25° C. and about 50% solids content in ethyl acetate of from about 1,200 cP to about 1,800 cP, preferably as measured using a Brookfield RVT viscometer equipped with a spindle number 5 at 50 RPM.
69. The transdermal therapeutic system according to any one of items 51 to 68,
wherein the silicone acrylic hybrid pressure-sensitive adhesive is characterized by a solution viscosity at 25° C. and about 50% solids content in ethyl acetate of from about 1,500 cP, preferably as measured using a Brookfield RVT viscometer equipped with a spindle number 5 at 50 RPM.
70. The transdermal therapeutic system according to any one of items 51 to 67,
wherein the silicone acrylic hybrid pressure-sensitive adhesive is characterized by a solution viscosity at 25° C. and about 50% solids content in ethyl acetate of from about 2,200 cP to about 2,800 cP, preferably as measured using a Brookfield RVT viscometer equipped with a spindle number 5 at 50 RPM.
71. The transdermal therapeutic system according to item 70,
wherein the silicone acrylic hybrid pressure-sensitive adhesive is characterized by a solution viscosity at 25° C. and about 50% solids content in ethyl acetate of about 2,500 cP, preferably as measured using a Brookfield RVT viscometer equipped with a spindle number 5 at 50 RPM.
72. The transdermal therapeutic system according to any one of items 51 to 71,
wherein the silicone acrylic hybrid pressure-sensitive adhesive is characterized by a complex viscosity at 0.1 rad/s at 30° C. of less than about 1.0e9 Poise, preferably as measured using a Rheometrics ARES rheometer, wherein the rheometer is equipped with 8 mm plates and the gap zeroed.
73. The transdermal therapeutic system according to any one of items 51 to 72,
wherein the silicone acrylic hybrid pressure-sensitive adhesive is characterized by a complex viscosity at 0.1 rad/s at 30° C. of from about 1.0e5 Poise to about 9.0e8 Poise, preferably as measured using a Rheometrics ARES rheometer, wherein the rheometer is equipped with 8 mm plates and the gap zeroed.
74. The transdermal therapeutic system according to any one of items 51 to 73,
wherein the silicone acrylic hybrid pressure-sensitive adhesive is characterized by a complex viscosity at 0.1 rad/s at 30° C. of from about 9.0e5 Poise to about 1.0e7 Poise, preferably as measured using a Rheometrics ARES rheometer, wherein the rheometer is equipped with 8 mm plates and the gap zeroed.
75. The transdermal therapeutic system according to any one of items 51 to 74,
wherein the silicone acrylic hybrid pressure-sensitive adhesive is characterized by a complex viscosity at 0.1 rad/s at 30° C. of from about 9.0e5 Poise to about 7.0e6 Poise, preferably as measured using a Rheometrics ARES rheometer, wherein the rheometer is equipped with 8 mm plates and the gap zeroed.
76. The transdermal therapeutic system according to any one of items 51 to 75,
wherein the silicone acrylic hybrid pressure-sensitive adhesive is characterized by a complex viscosity at 0.1 rad/s at 30° C. of about 4.0e6 Poise, preferably as measured using a Rheometrics ARES rheometer, wherein the rheometer is equipped with 8 mm plates and the gap zeroed.
77. The transdermal therapeutic system according to any one of items 51 to 73,
wherein the silicone acrylic hybrid pressure-sensitive adhesive is characterized by a complex viscosity at 0.1 rad/s at 30° C. of from about 2.0e6 Poise to about 9.0e7 Poise, preferably as measured using a Rheometrics ARES rheometer, wherein the rheometer is equipped with 8 mm plates and the gap zeroed.
78. The transdermal therapeutic system according to any one of items 51 to 73,
wherein the silicone acrylic hybrid pressure-sensitive adhesive is characterized by a complex viscosity at 0.1 rad/s at 30° C. of from about 8.0e6 Poise to about 9.0e7 Poise, preferably as measured using a Rheometrics ARES rheometer, wherein the rheometer is equipped with 8 mm plates and the gap zeroed.
79. The transdermal therapeutic system according to item 78,
wherein the silicone acrylic hybrid pressure-sensitive adhesive is characterized by a complex viscosity at 0.1 rad/s at 30° C. of about 1.0e7 Poise, preferably as measured using a Rheometrics ARES rheometer, wherein the rheometer is equipped with 8 mm plates and the gap zeroed.
80. The transdermal therapeutic system according to any one of items 1 to 79,
wherein the solifenacin-containing layer structure comprises a blend of at least two silicone acrylic hybrid pressure-sensitive adhesives which are characterized by different solution viscosities and/or by different complex viscosities.
81. The transdermal therapeutic system according to any one of items 1 to 80,
wherein the solifenacin-containing layer structure comprises at least one polyisobutylene.
82. The transdermal therapeutic system according to item 81,
wherein the polyisobutylene is a high molecular weight polyisobutylene having a viscosity average molecular weight $M_v$ of from about 800,000 to about 1,500,000, and a weight average molecular weight $M_w$ of from about 1,000,000 to about 1,700,000.
83. The transdermal therapeutic system according to item 81,
wherein the polyisobutylene is a low molecular weight polyisobutylene having a viscosity average molecular weight $M_v$ of from about 20,000 to about 60,000, and a weight average molecular weight $M_w$ of from about 25,000 to about 75,000.
84. The transdermal therapeutic system according to any one of items 1 to 83,
wherein the solifenacin-containing layer structure comprises a blend of at least two polyisobutylenes which are characterized by different viscosity average molecular weights and/or weight average molecular weights.
85. The transdermal therapeutic system according to any one of items 1 to 84,
wherein the solifenacin-containing layer structure comprises at least one acrylate polymer.
86. The transdermal therapeutic system according to item 85,
wherein the acrylate polymer is an acrylate-based pressure-sensitive adhesive.

87. The transdermal therapeutic system according to item 86,
wherein the acrylate-based pressure-sensitive adhesive is based on monomers selected from one or more of acrylic acid, butylacrylate, 2-ethylhexylacrylate, glycidylmethacrylate, 2-hydroxyethylacrylate, methylacrylate, methylmethacrylate, t-octylacrylamide and vinylacetate.

88. The transdermal therapeutic system according to item 86, wherein the acrylate-based pressure-sensitive adhesive is based on monomers selected from two or more of acrylic acid, butylacrylate, 2-ethylhexylacrylate, glycidylmethacrylate, 2-hydroxyethylacrylate, methylacrylate, methylmethacrylate, t-octylacrylamide and vinylacetate.

89. The transdermal therapeutic system according to any one of items 86 to 88,
wherein the acrylate-based pressure-sensitive adhesive is based on 2-ethylhexylacrylate, 2-hydroxyethylacrylate, and vinylacetate.

90. The transdermal therapeutic system according to any one of items 86 to 88,
wherein the acrylate-based pressure-sensitive adhesive is based on acrylic acid, butylacrylate, and 2-ethylhexylacrylate.

91. The transdermal therapeutic system according to any one of items 86 to 88,
wherein the acrylate-based pressure-sensitive adhesive is based on acrylic acid, 2-ethylhexylacrylate, glycidylmethacrylate, and methylacrylate.

92. The transdermal therapeutic system according to any one of items 1 to 91,
wherein the solifenacin is contained in an amount of from 2% to 40% by weight based on the solifenacin-containing layer.

93. The transdermal therapeutic system according to any one of items 1 to 92,
wherein the solifenacin is contained in an amount of from 3% to 40% by weight based on the solifenacin-containing layer.

94. The transdermal therapeutic system according to any one of items 1 to 93, wherein the solifenacin is contained in an amount of from 5% to 35% by weight based on the solifenacin-containing layer.

95. The transdermal therapeutic system according to any one of items 1 to 94,
wherein the solifenacin-containing layer structure contains 0.1 mg/cm$^2$ to 5.0 mg/cm$^2$ solifenacin based on the solifenacin-containing layer.

96. The transdermal therapeutic system according to any one of items 1 to 95,
wherein the solifenacin-containing layer structure contains 0.1 mg/cm$^2$ to 4.0 mg/cm$^2$ solifenacin based on the solifenacin-containing layer.

97. The transdermal therapeutic system according to any one of items 1 to 96,
wherein the solifenacin-containing layer structure contains 0.2 mg/cm$^2$ to 4.0 mg/cm$^2$ solifenacin based on the solifenacin-containing layer.

98. The transdermal therapeutic system according to any one of items 1 to 97, wherein the solifenacin is dispersed or dissolved in the solifenacin-containing layer.

99. The transdermal therapeutic system according to any one of items 1 to 98,
wherein the solifenacin-containing layer is obtainable by coating and drying a solifenacin-containing coating composition that comprises a therapeutically effective amount of solifenacin base, and preferably the at least one polymer.

100. The transdermal therapeutic system according to any one of items 1 to 99,
wherein the solifenacin is present in the form of the free base.

101. The transdermal therapeutic system according to any one of items 1 to 100, wherein the solifenacin-containing layer structure comprises an additional active agent.

102. The transdermal therapeutic system according to item 101, wherein the additional active agent is contained in the solifenacin-containing layer.

103. The transdermal therapeutic system according to item 101, wherein the solifenacin-containing layer structure comprises an additional skin contact layer comprising the additional active agent.

104. The transdermal therapeutic system according to any one of items 101 to 103, wherein the additional active agent is rivastigmine, preferably in the form of a free base.

105. The transdermal therapeutic system according to any one of items 1 to 104,
wherein the solifenacin-containing layer further comprises an auxiliary polymer.

106. The transdermal therapeutic system according to item 105,
wherein the auxiliary polymer is contained in an amount of from about 0.5% to about 20% by weight based on the solifenacin-containing layer.

107. The transdermal therapeutic system according to item 105 or 106,
wherein the auxiliary polymer is contained in an amount of from about 0.5% to about 10% by weight based on the solifenacin-containing layer.

108. The transdermal therapeutic system according to items 105 to 107,
wherein the auxiliary polymer is contained in an amount of from about 1% to about 5% by weight based on the solifenacin-containing layer.

109. The transdermal therapeutic system according to any one of items 105 to 108,
wherein said auxiliary polymer is selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof.

110. The transdermal therapeutic system according to any one of items 1 to 109, which provides a mean release rate of solifenacin of 2 to 12 mg/day, preferably of 3 to 10 mg/day, and more preferably of 3.5 to 6.75 mg/day, preferably over at least 24 hours, at least 48 hours, at least 72 hours, or 84 hours of administration.

111. The transdermal therapeutic system according to any one of items 1 to 110, which provides a cumulative permeated amount of solifenacin as measured in a Franz diffusion cell with dermatomed human skin of about 0.1 mg/cm$^2$ to about 2.0 mg/cm$^2$, preferably of about 0.2 mg/cm$^2$ to about 1.5 mg/cm$^2$, more preferably of 0.3 mg/cm$^2$ to 1.2 mg/cm$^2$ over a time period of 72 hours.

112. The transdermal therapeutic system according to any one of items 1 to 111, which provides a cumulative skin permeation rate of solifenacin over 72 hours as measured in a Franz diffusion cell with dermatomed human skin of about 1 µg/cm²-hr to about 30 µg/cm²-hr, preferably of about 2 µg/cm²-hr to about 20 µg/cm²-hr, more preferably of about 3 µg/cm²-hr to about µg/cm²-hr.

113. The transdermal therapeutic system according to any one of items 1 to 112, which releases more than 25% by weight of the amount of solifenacin contained in the transdermal therapeutic system over a period of administration of 72 hours, preferably determined by measuring the permeated amount of solifenacin in a Franz diffusion cell with dermatomed human skin with a thickness of 500 µm, when a phosphate buffer solution pH5.5 with 0.1% saline azide as antibacteriological agent is used at a temperature of 32±1° C.

114. The transdermal therapeutic system according to item 113, which releases more than 30% by weight of the amount of solifenacin contained in the transdermal therapeutic system over a period of administration of 72 hours.

115. The transdermal therapeutic system according to item 113, which releases more than 50% by weight of the amount of solifenacin contained in the transdermal therapeutic system over a period of administration of 72 hours.

116. The transdermal therapeutic system according to item 113, which releases more than 70% by weight of the amount of solifenacin contained in the transdermal therapeutic system over a period of administration of 72 hours.

117. The transdermal therapeutic system according to any one of items 1 to 116, for use in a method of treatment.

118. The transdermal therapeutic system according to any one of items 1 to 116, for use in a method of treating overactive bladder with symptoms of urge urinary incontinence, urgency, and urinary frequency.

119. The transdermal therapeutic system according to any one of items 1 to 116, wherein the solifenacin-containing layer structure comprises a therapeutically effective amount of rivastigmine in addition to the solifenacin, for use in a method of preventing, treating, or delaying of progression of Alzheimer's disease, dementia associated with Parkinson's disease, and/or symptoms of traumatic brain injury.

120. The transdermal therapeutic system according to any one of items 1 to 116,
wherein the solifenacin-containing layer structure comprises a therapeutically effective amount of rivastigmine in addition to the solifenacin, for use in a method of treating mild to moderate dementia caused by Alzheimer's or Parkinson's disease.

121. The transdermal therapeutic system according to any one of items 1 to 116, for use in a method of treatment, wherein the transdermal therapeutic system is applied on the skin of a patient for at least or about 24 hours, for more than 24 hours, for at least or about 48 hours, for at least or about 72 hours, or for about 84 hours.

122. Use of a transdermal therapeutic system according to any one of items 1 to 116, for the manufacture of a medicament.

123. Use of a transdermal therapeutic system according to any one of items 1 to 116, for the manufacture of a medicament for treating overactive bladder with symptoms of urge urinary incontinence, urgency, and urinary frequency.

124. Use of a transdermal therapeutic system according to any one of items 1 to 116,
wherein the solifenacin-containing layer structure comprises a therapeutically effective amount of rivastigmine in addition to the therapeutically effective amount of solifenacin, for the manufacture of a medicament for preventing, treating, or delaying of progression of Alzheimer's disease, dementia associated with Parkinson's disease, and/or symptoms of traumatic brain injury.

125. Use of a transdermal therapeutic system according to any one of items 1 to 116,
wherein the solifenacin-containing layer structure comprises a therapeutically effective amount of rivastigmine in addition to the therapeutically effective amount of solifenacin, for the manufacture of a medicament for treating mild to moderate dementia caused by Alzheimer's or Parkinson's disease.

126. Use of a transdermal therapeutic system according to any one of items 1 to 116, for the manufacture of a medicament that is applied to the skin of a patient for at least of about 24 hours, for more than 24 hours, for at least or about 48 hours, for at least or about 72 hours, or for about 84 hours.

127. A method of reducing the peripheral side effects induced by rivastigmine by applying to the skin of a patient a transdermal therapeutic system according to any one of items 1 to 116, preferably for at least of about 24 hours, for more than 24 hours, for at least or about 48 hours, for at least or about 72 hours, or for about 84 hours.

128. A method of treatment by applying to the skin of a patient a transdermal therapeutic system according to any one of items 1 to 116.

129. A method of treating overactive bladder with symptoms of urge urinary incontinence, urgency, and urinary frequency by applying to the skin of a patient a transdermal therapeutic system according to any one of items 1 to 116.

130. A method of preventing, treating, or delaying of progression of Alzheimer's disease, dementia associated with Parkinson's disease, and/or symptoms of traumatic brain injury by applying to the skin of a patient a transdermal therapeutic system according to any one of items 1 to 116, wherein the solifenacin-containing layer structure comprises a therapeutically effective amount of rivastigmine in addition to the therapeutically effective amount of solifenacin.

131. A method of treating mild to moderate dementia caused by Alzheimer's or Parkinson's disease by applying to the skin of a patient a transdermal therapeutic system according to any one of items 1 to 116, wherein the solifenacin-containing layer structure comprises a therapeutically effective amount of rivastigmine in addition to the therapeutically effective amount of solifenacin.

132. A method of treatment by applying to the skin of a patient a transdermal therapeutic system according to any one of items 1 to 116 for at least of about 24 hours, for more than 24 hours, for at least or about 48 hours, for at least or about 72 hours, or for about 84 hours.

133. A method of manufacture of a transdermal therapeutic system according to any one of items 1 to 116 comprising the steps of:

1) providing a solifenacin-containing coating composition comprising
   a) solifenacin and optionally an additional active agent,
   b) optionally a solvent,
2) coating the solifenacin-containing coating composition onto a release liner in an amount to provide the desired area weight,
3) drying the coated solifenacin-containing coating composition to provide the solifenacin-containing layer,
4) laminating the solifenacin-containing layer to a backing layer to provide an solifenacin-containing layer structure,
5) optionally providing an additional skin contact layer by coating and drying an active agent-free coating composition or an active agent-containing coating composition according to steps 2 and 3, removing the release liner of the solifenacin-containing layer and laminating the adhesive side of the skin contact layer onto the adhesive side of the solifenacin-containing layer to provide an solifenacin-containing layer structure,
6) punching the individual systems from the solifenacin-containing layer structure,
7) optionally adhering to the individual systems an active agent-free self-adhesive layer structure comprising also a backing layer and an active agent-free pressure-sensitive adhesive layer and which is larger than the individual systems of the solifenacin-containing layer structure, wherein at least one polymer is added to the solifenacin-containing coating composition in step 1, or, if an additional skin contact layer is provided, to the coating composition in step 5, or to both the solifenacin-containing coating composition in step 1 and to the coating composition in step 5.

134. A transdermal therapeutic system for the transdermal administration of solifenacin comprising a solifenacin-containing layer structure, the solifenacin-containing layer structure comprising:
A) a backing layer, and
B) a solifenacin-containing layer;
   wherein the solifenacin-containing layer comprises
   a) a therapeutically effective amount of solifenacin, and
   b) at least one polymer selected from the group consisting of a silicone pressure-sensitive adhesive and a silicone acrylic hybrid pressure-sensitive adhesive in an amount of from about 20% to about 99% by weight based on the solifenacin-containing layer,
wherein the transdermal therapeutic system does not contain a transdermal permeation enhancer selected from the group consisting of a fatty acid ester, a terpene, and a carboxylic acid having 2 to 10 carbon atoms.

135. A transdermal therapeutic system for the transdermal administration of solifenacin comprising a solifenacin-containing layer structure,
the solifenacin-containing layer structure comprising:
A) a backing layer,
B) a solifenacin-containing layer,
   wherein the solifenacin-containing layer comprises
   a) a therapeutically effective amount of solifenacin,
   b) at least one acrylate polymer, and
   c) optionally an additional active agent,
C) a skin contact layer comprising at least one polymer selected from the group consisting of a silicone pressure-sensitive adhesive and a silicone acrylic hybrid pressure-sensitive adhesive in an amount of from about 20% to about 100% by weight based on the solifenacin-containing layer,
wherein the transdermal therapeutic system does not contain a transdermal permeation enhancer selected from the group consisting of a fatty acid ester, a terpene, and a carboxylic acid having 2 to 10 carbon atoms.

136. A transdermal therapeutic system for the transdermal administration of solifenacin comprising a solifenacin-containing layer structure, the solifenacin-containing layer structure comprising:
A) a backing layer,
B) a solifenacin-containing layer,
   wherein the solifenacin-containing layer comprises
   a) a therapeutically effective amount of solifenacin,
   b) at least one polymer selected from the group consisting of a polymer based on polysiloxanes, a silicone acrylic hybrid polymer, a polymer based on polyisobutylenes, a styrene-isoprene-styrene block copolymer, and an acrylate polymer, and
   c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof,
C) optionally a skin contact layer,
wherein the transdermal therapeutic system does not contain a transdermal permeation enhancer selected from the group consisting of a fatty acid ester, a terpene, and a carboxylic acid having 2 to 10 carbon atoms.

137. A transdermal therapeutic system for the transdermal administration of solifenacin comprising a solifenacin-containing layer structure, the solifenacin-containing layer structure comprising:
A) a backing layer, and
B) a solifenacin-containing matrix layer;
   wherein the solifenacin-containing matrix layer comprises
   a) a therapeutically effective amount of solifenacin (e.g. solifenacin base), and
   b) at least one polymer selected from the group consisting of a polymer based on polysiloxanes and a silicone acrylic hybrid polymer,
wherein the transdermal therapeutic system does not contain a fatty acid ester, a terpene, and a carboxylic acid having 2 to 10 carbon atoms.

138. A transdermal therapeutic system for the transdermal administration of solifenacin comprising a solifenacin-containing layer structure, the solifenacin-containing layer structure comprising:
A) a backing layer, and
B) a solifenacin-containing matrix layer;
   wherein the solifenacin-containing matrix layer comprises
   a) a therapeutically effective amount of solifenacin (e.g. solifenacin base), and b) at least one polymer selected from the group consisting of a polymer based on polysiloxanes and a silicone acrylic hybrid polymer, wherein the transdermal therapeutic system does not contain a permeation enhancer.

139. A transdermal therapeutic system for the transdermal administration of solifenacin comprising a solifenacin-containing layer structure, the solifenacin-containing layer structure comprising:
A) a backing layer, and
B) a solifenacin-containing matrix layer;
wherein the solifenacin-containing matrix layer comprises
a) a therapeutically effective amount of solifenacin (e.g. solifenacin base), and
b) at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer,
wherein the transdermal therapeutic system does not contain a fatty acid ester, a terpene, and a carboxylic acid having 2 to 10 carbon atoms.

140. A transdermal therapeutic system for the transdermal administration of solifenacin comprising a solifenacin-containing layer structure, the solifenacin-containing layer structure comprising:
A) a backing layer, and
B) a solifenacin-containing matrix layer;
wherein the solifenacin-containing matrix layer comprises
a) a therapeutically effective amount of solifenacin (e.g. solifenacin base), and
b) at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer,
wherein the transdermal therapeutic system does not contain a permeation enhancer.

141. A transdermal therapeutic system for the transdermal administration of solifenacin comprising a solifenacin-containing layer structure, the solifenacin-containing layer structure comprising:
A) a backing layer, and
B) a solifenacin-containing matrix layer;
wherein the solifenacin-containing matrix layer comprises
a) a therapeutically effective amount of solifenacin (e.g. solifenacin base), and
b) a blend of a polymer based on polysiloxanes and an acrylate polymer,
c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof,
wherein the transdermal therapeutic system does not contain a fatty acid ester, a terpene, and a carboxylic acid having 2 to 10 carbon atoms.

142. A transdermal therapeutic system for the transdermal administration of solifenacin comprising a solifenacin-containing layer structure, the solifenacin-containing layer structure comprising:
A) a backing layer, and
B) a solifenacin-containing matrix layer;
wherein the solifenacin-containing matrix layer comprises
a) a therapeutically effective amount of solifenacin (e.g. solifenacin base), and
b) a blend of a polymer based on polysiloxanes and an acrylate polymer,
c) at least one auxiliary polymer selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof,
wherein the transdermal therapeutic system does not contain a permeation enhancer.

The invention claimed is:

1. A transdermal therapeutic system for the transdermal administration of solifenacin comprising a solifenacin-containing layer structure,
the solifenacin-containing layer structure comprising:
A) a backing layer, and
B) a solifenacin-containing layer comprising a therapeutically effective amount of solifenacin base,
wherein the solifenacin-containing layer structure comprises at least one polymer selected from the group consisting of a polymer based on polysiloxanes, a silicone acrylic hybrid polymer, a polymer based on polyisobutylenes, and an acrylate polymer, and wherein the transdermal therapeutic system does not contain a transdermal permeation enhancer selected from the group consisting of a fatty acid ester, a terpene, and a carboxylic acid having 2 to 10 carbon atoms; and
wherein the transdermal therapeutic system releases more than 25% of the solifenacin base contained in the transdermal therapeutic system over a period of administration of 72 hours.

2. The transdermal therapeutic system according to claim 1,
wherein the transdermal therapeutic system does not contain a transdermal permeation enhancer.

3. The transdermal therapeutic system according to claim 1,
wherein the solifenacin-containing layer comprises from about 20% to about 99% of the at least one polymer by weight of the solifenacin-containing layer.

4. The transdermal therapeutic system according to claim 1, wherein the solifenacin-containing layer is a solifenacin-containing matrix layer.

5. The transdermal therapeutic system according to claim 1,
wherein the solifenacin-containing layer structure comprises at least one polymer selected from the group consisting of a polymer based on polysiloxanes and a silicone acrylic hybrid polymer, and a further polymer selected from the group consisting of a polymer based on polysiloxanes, a silicone acrylic hybrid polymer, and an acrylate polymer.

6. The transdermal therapeutic system according to claim 1, wherein the solifenacin-containing layer is selected from the group consisting of:
(i) a solifenacin-containing layer comprising a blend of at least two polymers based on polysiloxanes having different physical properties;
(ii) a solifenacin-containing layer comprising a blend of a polymer based on polysiloxanes and an acrylate polymer;
(iii) a solifenacin-containing layer comprising a blend of at least two silicone acrylic hybrid polymers having different physical properties;
(iv) a solifenacin-containing layer comprising a blend of a silicone acrylic hybrid polymer and a polymer based on polysiloxanes;
(v) a solifenacin-containing layer comprising a blend of a silicone acrylic hybrid polymer and an acrylate polymer; and
(vi) a solifenacin-containing layer comprising a blend of at least two polyisobutylenes having different physical properties.

7. The transdermal therapeutic system according to claim 1,
wherein the solifenacin-containing layer is a skin contact layer.

8. The transdermal therapeutic system according to claim 1,
wherein the solifenacin-containing layer structure comprises an additional skin contact layer, and wherein the additional skin contact layer comprises the at least one polymer.

9. The transdermal therapeutic system according to claim 1,
wherein the solifenacin-containing layer structure comprises an additional skin contact layer, and wherein both the solifenacin-containing layer and the skin contact layer comprise the at least one polymer.

10. The transdermal therapeutic system according to claim 8,
wherein the skin contact layer contains from about 20% to about 100% of the at least one polymer by weight of the skin contact layer.

11. The transdermal therapeutic system according to claim 1,
wherein the at least one polymer is a pressure-sensitive adhesive.

12. The transdermal therapeutic system according to claim 1,
wherein the solifenacin-containing layer structure contains $0.1 \text{ mg/cm}^2$ to $5.0 \text{ mg/cm}^2$ solifenacin base.

13. The transdermal therapeutic system according to claim 1,
wherein the solifenacin-containing layer structure further comprises an additional active agent.

14. The transdermal therapeutic system according to claim 13,
wherein the additional active agent is rivastigmine.

15. The transdermal therapeutic system according to claim 1,
wherein the solifenacin-containing layer further comprises from about 0.5% to about 20% of an auxiliary polymer by weight of the solifenacin-containing layer.

16. The transdermal therapeutic system according to claim 15, wherein said auxiliary polymer is selected from the group consisting of alkyl methacrylate copolymers, amino alkyl methacrylate copolymers, methacrylic acid copolymers, methacrylic ester copolymers, ammonioalkyl methacrylate copolymers, polyvinylpyrrolidones, vinylpyrrolidone-vinyl acetate copolymers, polyvinyl caprolactam-polyvinyl acetate-polyethylene glycol copolymer, and mixtures thereof.

17. A method of treating overactive bladder with symptoms of urge urinary incontinence, urgency, and urinary frequency, the method comprising applying the transdermal therapeutic system according to claim 1 to the skin of a patient in need thereof for at least about 24 hours.

18. A method of reducing peripheral side effects induced by rivastigmine, the method comprising applying the transdermal therapeutic system according to claim 1 to the skin of a patient in need thereof for at least about 24 hours.

19. A method of manufacturing the transdermal therapeutic system according to claim 1, the method comprising:
(A) providing a solifenacin-containing coating composition comprising
a) solifenacin base and optionally an additional active agent, and
b) optionally a solvent;
(B) coating the solifenacin-containing coating composition onto a release liner in an amount to provide the desired area weight;
(C) drying the coated solifenacin-containing coating composition to provide a solifenacin-containing layer;
(D) laminating the solifenacin-containing layer to a backing layer to provide a solifenacin-containing layer structure;
(E) optionally providing an additional skin contact layer by coating and drying an active agent-free coating composition or an active agent-containing coating composition according to (B) and (C), removing the release liner of the solifenacin-containing layer, and laminating the adhesive side of the skin contact layer onto the adhesive side of the solifenacin-containing layer to provide a solifenacin-containing layer structure;
(F) punching individual systems from the solifenacin-containing layer structure, and
(G) optionally adhering to the individual systems an active agent-free self-adhesive layer structure comprising a backing layer and an active agent-free pressure-sensitive adhesive layer that is larger than the individual systems of the solifenacin-containing layer structure,
wherein at least one polymer selected from the group consisting of a polymer based on polysiloxanes, a silicone acrylic hybrid polymer, a polymer based on polyisobutylenes, and an acrylate polymer is added to the solifenacin-containing coating composition in (A), to the coating composition in (E), or to both the solifenacin-containing coating composition in (A) and to the coating composition in (E).

20. A transdermal therapeutic system for the transdermal administration of solifenacin comprising a solifenacin-containing layer structure,
the solifenacin-containing layer structure comprising:
A) a backing layer; and
B) a solifenacin-containing matrix layer,
wherein the solifenacin-containing matrix layer comprises:
a) a therapeutically effective amount of solifenacin base; and
b) at least one polymer, wherein the polymer is a polymer based on polysiloxanes, a silicone acrylic hybrid polymer, or a combination thereof, wherein the transdermal therapeutic system does not contain a fatty acid ester, a terpene, and a carboxylic acid having 2 to 10 carbon atoms, and wherein the transdermal therapeutic system releases more than 25% of the solifenacin base contained in the transdermal therapeutic system over a period of administration of 72 hours.

21. A transdermal therapeutic system for the transdermal administration of solifenacin comprising a solifenacin-containing layer structure, the solifenacin-containing layer structure comprising:

A) a backing layer; and

B) a solifenacin-containing matrix layer,
wherein the solifenacin-containing matrix layer comprises:
a) a therapeutically effective amount of solifenacin base;
b) at least one polymer, wherein the polymer is a polymer based on polysiloxanes, a silicone acrylic hybrid polymer, or a combination thereof; and
c) a further polymer, wherein the further polymer is a polymer based on polysiloxanes, a silicone acrylic hybrid polymer, an acrylate polymer, or a combination thereof, wherein the transdermal therapeutic system does not contain a fatty acid ester, a terpene, and a carboxylic acid having 2 to 10 carbon atoms; and wherein the transdermal therapeutic system releases more than 25% of the solifenacin base contained in the transdermal therapeutic system over a period of administration of 72 hours.

\* \* \* \* \*